United States Patent
Poole et al.

(10) Patent No.: US 10,941,385 B2
(45) Date of Patent: Mar. 9, 2021

(54) MODIFIED MICROORGANISMS AS SUSTAINABLE SOURCES OF OMEGA-3 POLYUNSATURATED FATTY ACID PRODUCTION

(71) Applicant: Wake Forest University, Winston-Salem, NC (US)

(72) Inventors: Leslie B. Poole, Winston-Salem, NC (US); Floyd H. Chilton, Winston-Salem, NC (US); Derek Parsonage, Winston-Salem, NC (US); Susan Sergeant, Winston-Salem, NC (US)

(73) Assignee: Wake Forest University, Winston-Salem, NC (US)

( * ) Notice: Subject to any disclaimer, the term of this patent is extended or adjusted under 35 U.S.C. 154(b) by 32 days.

(21) Appl. No.: 16/336,027

(22) PCT Filed: Sep. 22, 2017

(86) PCT No.: PCT/US2017/052938
§ 371 (c)(1),
(2) Date: Mar. 22, 2019

(87) PCT Pub. No.: WO2018/057879
PCT Pub. Date: Mar. 29, 2018

(65) Prior Publication Data
US 2019/0367889 A1 Dec. 5, 2019

Related U.S. Application Data

(60) Provisional application No. 62/398,604, filed on Sep. 23, 2016.

(51) Int. Cl.
| | | |
|---|---|---|
| C12N 9/02 | (2006.01) | |
| A61K 31/201 | (2006.01) | |
| C12P 7/64 | (2006.01) | |
| C07K 14/195 | (2006.01) | |

(52) U.S. Cl.
CPC .......... *C12N 9/0071* (2013.01); *A61K 31/201* (2013.01); *C12P 7/6427* (2013.01); *C12Y 114/19* (2013.01)

(58) Field of Classification Search
None
See application file for complete search history.

(56) References Cited

U.S. PATENT DOCUMENTS

| | | | |
|---|---|---|---|
| 8,975,299 B2 * | 3/2015 | Bar Yosef | A61K 31/683 514/558 |
| 2011/0053216 A1 | 3/2011 | Vermaas | |
| 2013/0323801 A1 | 12/2013 | Chilton et al. | |

FOREIGN PATENT DOCUMENTS

WO    2010/057246 A1    5/2010

OTHER PUBLICATIONS

Gao Chen et al., "Transgenic expression of delta-6 and delta-15 fatty acid desaturases enhances omega-3 polyunsaturated fatty acid accumulation in *Synechocystis* sp. PCC6803", Biotechnology For Biofuels, Biomed Central Ltd, vol. 7, No. 1, 2014, p. 32.
Lingang Zhang et al., "Possible function of VIPP1 in maintaining chloroplast membranes", Biochimica et Biophysica ACTA. Bioenergetics., vol. 1847, No. 9, 2015, pp. 831-837.
The partial supplementary European search report dated Sep. 28, 2020 issued in Eurolpean Patent Application No. 17853981.3.
UniProtKB Accession No. B1XMW7 "VIPP1 protein", May 20, 2008 [located online Jan. 10, 2018 at http://www.uniprot.org/uniprot/B1XMW7).

* cited by examiner

*Primary Examiner* — Suzanne M Noakes
*Assistant Examiner* — Jae W Lee
(74) *Attorney, Agent, or Firm* — Fox Rothschild LLP

(57) ABSTRACT

The present invention relates to recombinant vectors, modified microorganisms, and methods for omega-3 polyunsaturated fatty acid production.

12 Claims, 8 Drawing Sheets
Specification includes a Sequence Listing.

MODIFIED MICROORGANISMS AS SUSTAINABLE SOURCES OF OMEGA-3 POLYUNSATURATED FATTY ACID PRODUCTION

CROSS REFERENCE TO RELATED APPLICATION

This application claims priority to U.S. Provisional Application No. 62/398,604 filed on Sep. 23, 2016. The content of the application is incorporated herein by reference in its entirety.

TECHNICAL FIELD

The presently disclosed subject matter pertains in some embodiments to the preparation and use of recombinant vectors and modified microorganisms for omega-3 polyunsaturated fatty acid production.

GENERAL CONSIDERATIONS

There is an enormous and growing demand for omega 3 (ω3) polyunsaturated fatty acids (PUFAs) in human dietary supplements, medical foods, pharmaceuticals and functional foods as well as fish and livestock feeds given their tremendous health benefits. Yet the primary source for ω3 PUFAs, fish oil, is already in limited supply, leading to significant commercial interest in developing new sources of ω3 PUFAs.

Over the past 50 years, a large body of evidence has shown that certain polyunsaturated fatty acids (PUFAs) (i.e., long chain (LC), Wω3 PUFAs) have the capacity to reduce both the incidence and severity, and in some cases treat, many of the developed world's most devastating diseases including heart disease, stroke, diabetes, arthritis, asthma, dermatitis, and cancer. These PUFAs are also recognized to be essential in both neonatal and early infant cognitive and behavioral development, and an emerging body of data suggests they likely play a role in reducing the risk of and in treating cognitive decline with aging, including Alzheimer's disease.

These promising results have created an enormous demand for ω3 PUFAs. For example, fish oil supplements recently surpassed multivitamins as the most consumed supplement in the world (2009 sales of $~3.0 billion). Additionally, there has been a worldwide effort to include ω3 PUFAs in infant formulas.

In the face of this dramatic expansion of ω3 demand, the global supply, for all its end uses, is not sustainable at current levels of fish and fish oil consumption. In fact, fisheries globally have reached a crisis, resulting in a dramatic increase in the price of fish oil (for animal and human consumption) and fish meal. Thus, both the United States and Europe have introduced legislation to reduce the use of fish products in animal feeds. If consumption continues at the same rate, commercially-exploited stocks of fish (and oil) will collapse by 2050.

Most plant-sourced ω3-containing oils, such as flax seed oil, contain the 18-carbon (18C-) PUFA, α-linolenic acid (ALA) (FIGS. 1 and 2). ALA can be converted to beneficial, biologically-active long chain (LC-) ω3 PUFAs utilizing desaturation and elongation enzymes. Most studies indicate that these enzymes worked equally as well on ω3 and ω6 PUFAs and only small quantities of 18C-PUFAs could be metabolized by this pathway to LC-PUFAs. Consequently, ALA is very poorly metabolized to long chain (LC) ω3 PUFAs, such as eicosapentaenoic acid (EPA) and docosahexaenoic acid (DHA) and these LC-PUFAs have the health benefits to humans.

The ω3 LC-PUFAs also contain a complex conjugated double bond structure that makes them highly susceptible to oxidation, giving rise to substantial stability and taste issues. As a result, providing a more stable alternative that humans and animals would metabolize to biologically-active ω3 LC-PUFAs is an object of the presently disclosed subject matter. In the ω3 LC PUFA biosynthesis pathway, the first metabolic step utilizing ALA in mammals is a Δ6 desaturase step (FIGS. 1 and 2) and numerous studies in humans illustrate that this step represents the rate-limiting (bottleneck) step for converting ALA in botanical oils to ω3 LC-PUFAs.

It was hypothesized that if plant seed oils containing the product of the Δ6 desaturase step, stearidonic acid (SDA), could be found, then this fatty acid would be efficiently converted to LC-PUFAs, and thus afford the same or similar benefits as ω3 LC-PUFAs found in fish oils. Such oils were found in relatively rare plant species of the Boraginaceae family, and SDA from these plant seed oils was shown to be efficiently converted to LC-PUFAs and had many of their same benefits as LC-PUFAs in humans (James et al., Am J Clin Nutr. 2003 May, 77(5):1140-1145; Surette et al., J Nutr. 2004 June, 134(6):1406-1411; and Whelan, J Nutr. 2009 January, 139(1):5-10). Based on this work, Monsanto began to genetically engineer soybeans and canola to shift the primary fatty acid profile from ω6-containing 18C-PUFAs to the ω3 PUFA, SDA. They succeeded in producing soybean oil that contained 16-23% of its total fatty acids as SDA. However, the need for large-scale farming operations may limit the usefulness of these crop plants. Thus, the feasibility of commercial application and the stability of these transgenic plant commodities remain to be determined. Yet numerous animal and human studies and at least two clinical trials over the past 5 years indicate that SDA-enhanced soybean oil can significantly elevate ω3 LC-PUFAs and improve markers of cardiovascular health (Harris, Am J Clin Nutr. 2008. 87(6):1997S-2002S; and Lemke et al., Am J Clin Nutr., 2010, 92(4):766-775).

Another focus of the industry (with regard to ω3 PUFA sustainability) has been microalgae. However, no one has ever used marine bacteria or cyanobacteria, each of which has major cost and capacity advantages over microalgae.

Accordingly, it is an object of the presently disclosed subject matter to provide a novel recombinant vector for use in modifying microorganisms for production of ω3 PUFAs, e.g., ω3 PUFAs highly enriched in SDA. This and other objects are achieved in whole or in part by the presently disclosed subject matter.

An object of the presently disclosed subject matter having been stated above, other objects and advantages will become apparent upon a review of the following descriptions, examples and figures.

SUMMARY

This invention addresses the needs described above by providing among others modified microorganisms for production of ω3 PUFAs (e.g., ω3 PUFAs highly enriched in SDA), related recombinant vectors, related lipid compositions, and related methods.

In one aspect, the invention provides a recombinant vector comprising a heterologous promoter operably linked to a nucleic acid sequence encoding a thylakoid-promoting protein Vipp1 and at least one nucleic acid sequence encoding a Δ6 desaturase or a ω3 desaturase (also known as a Δ15 desaturase). Optionally, the vector can comprise a back bone sequence affording compatibility with a plurality of microorganisms. The recombinant vector can comprise a heterologous promoter operably linked to a nucleic acid sequence encoding a thylakoid-promoting protein Vipp1, a nucleic acid sequence encoding a Δ6 desaturase, and a nucleic acid sequence encoding a ω3 desaturase.

The thylakoid-promoting protein Vipp1 can be encoded by a nucleic acid sequence comprising SEQ ID NO: 1, a nucleic acid sequence at least about 70% identical to SEQ ID NO: 1, or a nucleic acid sequence that encodes an amino acid sequence comprising SEQ ID NO: 6 or an amino acid sequence at least about 70% identical to SEQ ID NO:6. In some embodiments, the Vipp1 can have an amino acid sequence comprising SEQ ID NO: 6 or an amino acid sequence at least about 70% identical to SEQ ID NO: 6.

The desaturase can be encoded by a nucleic acid sequence comprising a sequence selected from the group comprising SEQ ID NOs: 2 and 3, a nucleic acid sequence at least about 70% identical to SEQ ID NOs: 2 or 3, or a nucleic acid sequence that encodes an amino acid sequence comprising SEQ ID NO: 5 or 7 or an amino acid sequence at least about 70% identical to SEQ ID NO: 5 or 7. In some embodiments, the desaturase can comprise an amino acid sequence selected from SEQ ID NOs: 5 and 7 or an amino acid sequence at least about 70% identical to SEQ ID NOs: 5 or 7.

The thylakoid-promoting protein Vipp1, Δ6 desaturase, and 3 desaturase can be each encoded by a nucleic acid sequence comprising SEQ ID NO: 4 or a nucleic acid sequence at least about 70% identical to SEQ ID NO: 4 and/or another nucleic acid sequence encoding at least SEQ ID NOs: 5, 6, and 7 or encoding amino acid sequences that are at least 70% identical to SEQ ID NOs: 5, 6, and 7.

In some embodiments, the nucleic acid sequence encoding a thylakoid-promoting protein Vipp1, the nucleic acid sequence encoding a Δ6 desaturase, and/or the nucleic acid sequence encoding a ω3 desaturase can be a natural gene sequence or a synthetic gene sequence. The recombinant vector described above can be compatible with a cyanobacterium. Examples of the cyanobacterium include species of *Anabaena, Leptolyngbya, Lyngbya, Nostoc, Phormidium, Spirulina, Synechococcus*, or *Synechocystis*. The recombinant vector can further comprise one or more sequences affording expression or transcription control.

In a second aspect, the invention provides a lipid composition having lipid profile comprising lipids and at least about 15% or more stearidonic acid (SDA). Also provided is a lipid composition having a lipid profile comprising lipids and an 3 fatty acid selected from the group comprising or consisting of α-linolenic acid (ALA), stearidonic acid (SDA), and/or ω3 arachidonic acid (ETAω3), and/or any combination thereof. In the lipid composition, the lipid profile can comprise at least about 25%, 30%, or 35% 3 fatty acids. The lipid profile can comprise at least about 9% ALA, at least about 15% SDA, and/or at least about 1% ETAω3. The lipids can comprise glycolipids, phospholipids, triglycerides or combinations thereof, optionally the glycolipids are present in a greater amount than the phospholipids and triglycerides, or optionally the glycolipids comprise galactolipids. In some embodiments, the lipid composition is produced by a modified cyanobacterium, such as a species of *Anabaena, Leptolyngbya, Lyngbya, Nostoc, Phormidium, Spirulina, Synechococcus*, or *Synechocystis*.

In a third aspect, the invention provides a modified microorganism comprising a first exogenous gene encoding a thylakoid-promoting protein Vipp1. The modified microorganism can further comprise at least a second exogenous gene encoding a desaturase. The modified microorganism produces a lipid in a greater amount than does a control microorganism identical in all respects except that it does not include the first exogenous gene encoding thylakoid-promoting protein Vipp1 and the second exogenous gene encoding a desaturase. The modified microorganism can comprise at least two exogenous genes encoding a desaturase, where each gene encodes a different desaturase. The desaturase can be Δ6 desaturase or ω3 desaturase. For example, the first desaturase can be a Δ6 desaturase and the second desaturase can be a ω3 desaturase.

The thylakoid-promoting protein Vipp1 can be encoded by a nucleic acid sequence comprising SEQ ID NO: 1, a nucleic acid sequence at least about 70% identical to SEQ ID NO: 1, or a nucleic acid sequence that encodes an amino acid sequence comprising SEQ ID NO: 6 or an amino acid sequence at least about 70% identical to SEQ ID NO:6. The Vipp1 can comprise an amino acid sequence comprising SEQ ID NO: 6 or an amino acid sequence at least about 70% identical to SEQ ID NO: 6.

The desaturase can be encoded by a nucleic acid sequence comprising a sequence selected from the group comprising SEQ ID NOs: 2 and 3, a nucleic acid sequence at least about 70% identical to SEQ ID NOs: 2 or 3, or a nucleic acid sequence that encodes an amino acid sequence comprising SEQ ID NO: 5 or 7 or an amino acid sequence at least about 70% identical to SEQ ID NO: 5 or 7. The desaturase can comprise an amino acid sequence selected from the group comprising SEQ ID NOs: 5 and 7 or an amino acid sequence at least about 70% identical to one of SEQ ID NOs: 5 or 7.

The thylakoid-promoting protein Vipp1, Δ6 desaturase, and ω3 desaturase can be each encoded by a nucleic acid sequence comprising SEQ ID NO: 4 or a nucleic acid sequence at least about 70% identical to SEQ ID NO: 4 or another nucleic acid sequence that encodes amino acid sequences comprising each of SEQ ID NOs: 5, 6, and 7 or amino acid sequences that are at least about 70% identical to SEQ ID NOs: 5, 6, and 7.

The nucleic acid sequence encoding a thylakoid-promoting protein Vipp1, the nucleic acid sequence encoding a Δ6 desaturase, and/or the nucleic acid sequence encoding a 03 desaturase can be a natural gene sequence or a synthetic gene sequence. The modified microorganism can be a cyanobacterium, e.g., a species of *Anabaena, Leptolyngbya, Lyngbya, Nostoc, Phormidium, Spirulina, Synechococcus* or *Synechocystis*.

In a fourth aspect, the invention provides a method of culturing a lipid-producing microorganism. The method includes (i) providing a culture of a modified microorganism that comprises an exogenous gene encoding thylakoid-promoting protein Vipp1 and at least one exogenous gene encoding a desaturase and (ii) maintaining the microorganism or its progeny in a suitable culture medium under conditions in which the exogenous gene encoding the thylakoid-promoting protein Vipp1 and the exogenous gene encoding the desaturase are expressed. The culture produces a greater amount of the lipid than does a culture comprising a control microorganism identical in all respects except that it does not include the gene encoding a exogenous thylakoid-promoting protein Vipp1 and at least one exogenous gene encoding a desaturase. The modified microorganism can comprise at least two exogenous genes encoding a desaturase, where each gene encodes a different desaturase.

In the method, the desaturase can be Δ6 desaturase or ω3 desaturase. For example, the first desaturase can be a Δ6 desaturase and the second desaturase a ω3 desaturase. The thylakoid-promoting protein Vipp1 can be encoded by a nucleic acid sequence comprising SEQ ID NO: 1 or a nucleic acid sequence at least about 70% identical to SEQ ID NO: 1, or a nucleic acid sequence that encodes an amino acid sequence comprising SEQ ID NO: 6 or an amino acid sequence at least about 70% identical to SEQ ID NO: 6. In some examples, the Vipp1 comprises an amino acid sequence comprising SEQ ID NO: 6 or an amino acid sequence at least about 70% identical to SEQ ID NO: 6.

In the method, the desaturase can be encoded by a nucleic acid sequence comprising a sequence selected from the group comprising SEQ ID NOs: 2 and 3, or a nucleic acid sequence at least about 70% identical to SEQ ID NO: 2 or 3, or a nucleic acid sequence that encodes an amino acid sequence comprising SEQ ID NO: 5 or 7 or an amino acid sequence at least about 70% identical to SEQ ID NO: 5 or 7. In some example, the desaturase comprises an amino acid sequence comprising SEQ ID NO: 5 or SEQ ID NO: 7 or an amino acid sequence at least about 70% identical to SEQ ID NO: 5 or SEQ ID NO: 7.

In the method, the thylakoid-promoting protein Vipp1, Δ6 desaturase, and 3 desaturase can be each encoded by a nucleic acid sequence comprising SEQ ID NO:4 or a nucleic acid sequence at least about 70% identical to SEQ ID NO: 4 or a nucleic acid sequence that encodes amino acid sequences comprising each of SEQ ID Nos: 5, 6, and 7 or amino acid sequences at least about 70% identical to SEQ ID NOs: 5, 6, and 7.

The nucleic acid sequence encoding a thylakoid-promoting protein Vipp1, the nucleic acid sequence encoding a Δ6 desaturase, and/or the nucleic acid sequence encoding a O3 desaturase can be a natural gene sequence or a synthetic gene sequence. The modified microorganism can be a cyanobacterium such as a species of *Anabaena, Leptolyngbya, Lyngbya, Nostoc, Phormidium, Spirulina, Synechococcus* or *Synechocystis*.

The method described above can further comprise extracting a lipid composition from the culture.

In a further aspect, the invention provides a composition comprising a microorganism described above and/or an extract and/or processed product thereof. The composition can be in an administrable form selected from the group consisting of a pharmaceutical formulation, a nutritional formulation, a feed formulation, a dietary supplement, a medical food, a functional food, a beverage product and combinations thereof. The composition can be nutraceuticals, pharmaceuticals, dietary supplements, medical foods and functional foods. In some embodiments, the composition can be feeds and additives to food, including food for humans and for animal feed, e.g., feed for fish and/or for other animals, including but not limited to fowl, swine and cattle. The animal feed can be used for all animals utilizing these fatty acids including poultry, pork, beef, etc. In a further aspect, the invention provides a feed for use in aquaculture, optionally for use in farming various fish such as salmon and Tilapia, comprising a microorganism described above and/or an extract and/or a processed product thereof. Also provided are any and all methods, compositions, kits, reagents, devices, and/or systems shown and/or described expressly or by implication in the information provided herewith, including but not limited to features that may be apparent and/or understood by those of skill in the art.

DETAILED DESCRIPTION

Figure 1:
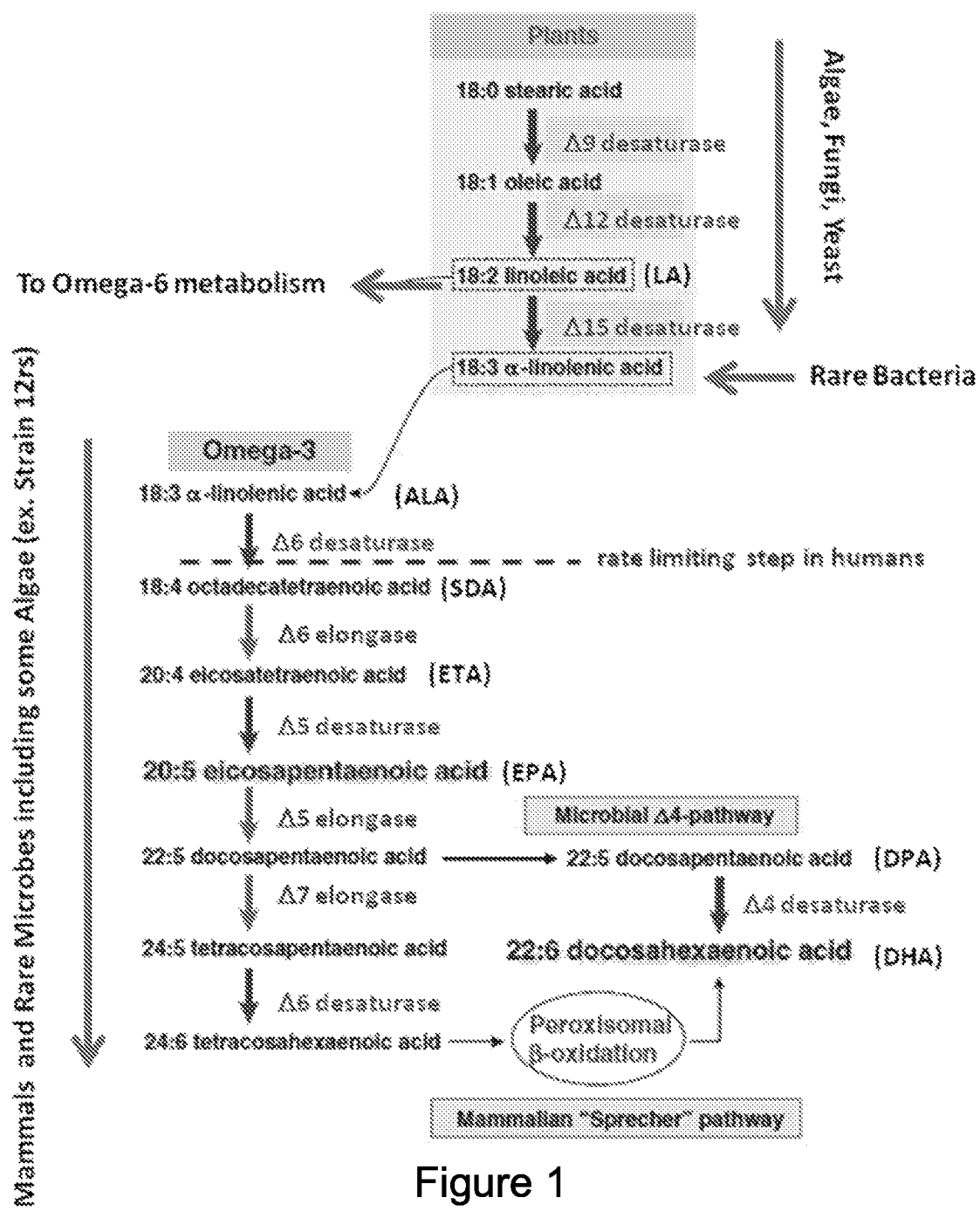
FIG. 1 is a schematic drawing focusing on omega-3 (ω3) long chain (LC) polyunsaturated fatty acid (PUFA) biosynthesis pathways and enzymes in mammals and rare microbes (FIG. 1 adapted from Napier et al., Ann. Rev. Plant Biol. (2007) 58:295).
Figure 2:
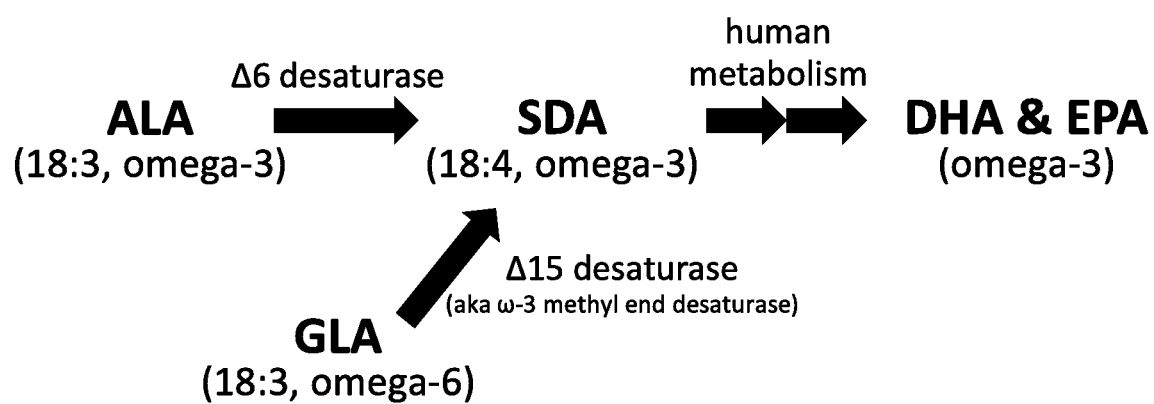
FIG. 2 is a schematic drawing showing a pathway for converting α-linolenic acid (ALA) and γ-linolenic acid (GLA) into omega-3 (ω3) long chain (LC) polyunsaturated fatty acids (PUFAs), such as docosahexaenoic acid (DHA) and eicosapentaenoic acid (EPA) via stearidonic acid (SDA) as an intermediate.

The presently disclosed subject matter will now be described more fully hereinafter with reference to the accompanying Figures and Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art. Certain components in the Figures are not necessarily to scale, emphasis instead being placed upon illustrating the principles of the presently disclosed subject matter (in some cases schematically).

While the following terms are believed to be well understood by one of ordinary skill in the art, the following definitions are set forth to facilitate explanation of the presently disclosed subject matter.

Following long-standing patent law convention, the terms "a" and "an" mean "one or more" when used in this application, including the claims.

Unless otherwise indicated, all numbers expressing quantities of size, biomarker concentration, probability, percentage and so forth used in the specification and claims are to be understood as being modified in all instances by the term "about". For example, the amounts can vary by about 10%, 5%, 1%, or 0.5%. Accordingly, unless indicated to the contrary, the numerical parameters set forth in this specification and attached claims are approximations that can vary depending upon the desired properties sought to be obtained by the presently disclosed subject matter.

The term "and/or" when used in describing two or more items or conditions refers to situations where all named items or conditions are present or applicable, or to situations wherein only one (or less than all) of the items or conditions is present or applicable.

The term "comprising", which is synonymous with "including," "containing," or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising," "consisting essentially of," and "consisting of", where one of these three terms is used herein, the presently disclosed and claimed subject matter can include the use of the other two terms.

"Exogenous gene" refers to a nucleic acid sequence that codes for the expression of an RNA and/or protein that has been introduced into a cell (e.g. by transformation/transfection), and is also referred to as a "transgene". A cell comprising an exogenous gene can be referred to as a recombinant cell, into which additional exogenous gene(s) can be introduced. The exogenous gene can be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene can be present in more than one copy in the cell. An exogenous gene can be a natural gene, e.g., excised from a natural source, or can be synthesized.

"In operable linkage", "operably linked", and grammatical variations thereof are used interchangeably herein to refer to a functional linkage between two nucleic acid sequences, such as a control sequence (typically a promoter) and the linked sequence (typically a sequence that encodes a protein, also called a coding sequence). A promoter is in operable linkage with an exogenous gene if it can mediate transcription/expression of the gene.

In connection with a lipid composition of the presently disclosed subject matter, a "profile" refers to the distribution of particular chemical species within the composition. In some embodiments, a "profile" refers to a % of a given PUFA relative to the total fatty acid concentration.

The term "percent sequence identity", in the context of two or more amino acid or nucleic acid sequences, refers to two or more sequences or subsequences that are the same or have a specified percentage of amino acid residues or nucleotides that are the same, when compared and aligned for maximum correspondence, as measured using a sequence comparison algorithm or by visual inspection. For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted using the NCBI BLAST software (ncbi.nlm.nih.gov/BLAST/) set to default parameters. For example, to compare two nucleic acid sequences, one may use blastn with the "BLAST 2 Sequences" tool Version 2.0.12 (Apr. 21, 2000) set at the following default parameters: Matrix: BLOSUM62; Reward for match: 1; Penalty for mismatch: −2; Open Gap: 5 and Extension Gap: 2 penalties; Gap.times.drop-off: 50; Expect: 10; Word Size: 11; Filter: on. For a pairwise comparison of two amino acid sequences, one may use the "BLAST 2 Sequences" tool Version 2.0.12 (Apr. 21, 2000) with blastp set, for example, at the following default parameters: Matrix: BLOSUM62; Open Gap: 11 and Extension Gap: 1 penalties; Gap.times.drop-off 50; Expect: 10; Word Size: 3; Filter: on.

"Recombinant" is a cell, nucleic acid, protein or vector that has been modified due to the introduction of an exogenous nucleic acid or the alteration of a native nucleic acid. Thus, e.g., recombinant cells can express genes that are not found within the native (non-recombinant) form of the cell or express native genes differently than those genes are expressed by a non-recombinant cell (e.g., overexpress a gene). Recombinant cells can, without limitation, include recombinant nucleic acids that encode for a gene product or for suppression elements such as mutations, knockouts, antisense, interfering RNA (RNAi) or dsRNA that reduce the levels of active gene product in a cell. A "recombinant nucleic acid" is a nucleic acid originally formed in vitro, in general, by the manipulation of nucleic acid, e.g., using polymerases, ligases, exonucleases, and endonucleases, using chemical synthesis, or otherwise is in a form not normally found in nature. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant for the purposes of the presently disclosed subject matter. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of the presently disclosed subject matter. Similarly, a "recombinant protein" is a protein made using recombinant techniques, i.e., through the expression of a recombinant nucleic acid.

I. Recombinant Vectors

Provided in accordance with some embodiments of the presently disclosed subject matter is a recombinant vector comprising a nucleic acid sequence encoding thylakoid-promoting protein Vipp1 and at least one nucleic acid sequence encoding a desaturase. In some embodiments, the recombinant vector comprises a nucleic acid sequence encoding a thylakoid-promoting protein Vipp1, a nucleic acid sequence encoding Δ6 desaturase, a nucleic acid sequence encoding ω3 (delta 15) desaturase, or any combination thereof. In some embodiments, the recombinant vector comprises a heterologous promoter operably linked to a nucleic acid sequence encoding a thylakoid-promoting protein Vipp1, a nucleic acid sequence encoding Δ6 desaturase, and/or a nucleic acid sequence encoding ω3 desaturase. In some embodiments, the recombinant vector comprises a backbone sequence affording compatibility with a plurality of microorganisms.

In some embodiments, the recombinant vector comprises a nucleic acid sequence encoding a thylakoid-promoting protein Vipp1, a nucleic acid sequence encoding Δ6 desaturase, and a nucleic acid sequence encoding ω3 desaturase operably oriented so that each polypeptide will be expressed. In some embodiments, in a suitable culture where each polypeptide is expressed, the culture produces a greater amount of one or more lipid compositions than does a control culture identical in all respects except that the polypeptides are not expressed or not expressed to a degree that they are expressed in the test culture. In some embodiments, the recombinant vector comprises one or more nucleic acid sequence(s) comprising one or more sequences affording expression or transcription control, such as a promoter sequence, a repressor sequence, a terminator sequence, a transcription blocking sequence, and combinations thereof. In some embodiments, the recombinant vector comprises a nucleic acid sequence coding for a selectable marker, such as antibiotic resistance.

In some embodiments, a recombinant vector in accordance with the presently disclosed subject matter comprises a plasmid. In some embodiments, a recombinant vector optimized for transformation of and/or expression in a microorganism is provided. In some embodiments, the microorganism is a cyanobacterium, a diverse phylum of oxygenic phototrophs in the kingdom bacteria. In some embodiments, the cyanobacterium is in the order Gloeobacterales. In some embodiments, the cyanobacterium is in the order Chroococcales. In some embodiments, the cyanobacterium is in the order Nostocales. In some embodiments, the cyanobacterium is in the order Oscillatoriales. In some embodiments, the cyanobacterium is in the order Pleurocapsales. In some embodiments, the cyanobacterium is in the order Prochlorales. In some embodiments, the cyanobacterium is in the order Stigonematales. In some embodiments, the cyanobacterium is unicellular. In some embodiments, the cyanobacterium is filamentous heterocystous. In some embodiments, the cyanobacterium is filamentous non-heterocystous. In some embodiments, the cyanobacterium is a freshwater strain. In some embodiments, the cyanobacterium is a marine strain. In some embodiments, the cyanobacterium is a species of *Anabaena, Leptolyngbya, Lyngbya, Nostoc, Phormidium, Spirulina, Synechococcus,* or *Synechocystis.*

In some embodiments, the nucleic acid sequence encoding a thylakoid-promoting protein Vipp1, the nucleic acid sequence encoding a Δ6 desaturase, and/or the nucleic acid sequence encoding a ω3 desaturase is a natural gene sequence. In some embodiments, the nucleic acid sequence encoding a thylakoid-promoting protein Vipp1, the nucleic acid sequence encoding a Δ6 desaturase, and/or the nucleic acid sequence encoding a ω3 desaturase is a synthetic gene sequence.

In some embodiments, the thylakoid-promoting protein Vipp1, Δ6 desaturase, and/or ω3 desaturase is/are homologous with respect to a microorganism to be transformed with the recombinant vector. In some embodiments, the thylakoid-promoting protein Vipp1, Δ6 desaturase, and/or ω3 desaturase is/are heterologous with respect to a microorganism to be transformed with the recombinant vector.

In some embodiments, the thylakoid-promoting protein Vipp1 is encoded by a nucleic acid sequence comprising SEQ ID NO: 1. However, the nucleic acid sequence can comprise any other sequence that encodes an amino acid sequence comprising SEQ ID NO:6. In some embodiments, the desaturase is encoded by a nucleic acid sequence comprising a sequence selected from the group comprising SEQ ID NOs: 2 and 3 or another nucleic acid sequence that encodes an amino acid sequence as set forth in SEQ ID NO:5 or SEQ ID NO:7. In some embodiments, the thylakoid-promoting protein Vipp1, Δ6 desaturase, and ω3 desaturase are each encoded by a single nucleic acid sequence, such as a nucleic acid sequence comprising SEQ ID NO: 4. However, the nucleic acid sequence can be any other single nucleic sequence that encodes each of SEQ ID NOs: 5, 6, and 7, wherein the nucleic acid sequences encoding SEQ INOs: 5, 6, and 7 can be arranged in any order within the larger nucleic acid sequence.

In some embodiments, a recombinant vector in accordance with the presently disclosed subject matter comprises a coding sequence comprising a nucleotide sequence of any of SEQ ID NOs: 1-4; or a coding sequence comprising a nucleotide sequence substantially identical to any of any of SEQ ID NOs: 1-4. In some embodiments, a recombinant vector in accordance with the presently disclosed subject matter comprises a coding sequence comprising a nucleotide sequence that is 70%, 75%, 80%, 85%, 90%, 91%, 92%, 93%, 94%, 95%, 96%, 97%, 98% or 99% identical to any of SEQ ID NOs: 1-4. In some embodiments, a recombinant vector in accordance with the presently disclosed subject matter comprises a coding sequence comprising a nucleotide sequence that encodes an amino acid sequence that is 70%, 75%, 80%, 85%, 90%, 91%, 92%, 93%, 94%, 95%, 96%, 97%, 98% or 99% identical to any of SEQ ID NOs: 5-7.

Referring now to Table 1 below and to FIG. 7, a representative embodiment of a recombinant vector in accordance with the presently disclosed subject matter is provided. The representative recombinant vector is a 13,611 bp plasmid that includes the pAM44148 expression vector describe in Taton et al. (2012) that contains both the lac1 repressor and trc promoter from E. coli, as well as synthetic genes for the delta 6 (Δ6) and omega 3 (ω3) desaturases and the vesicle-inducing protein in plastids (Vipp1).

TABLE 1

| Feature | Function |
|---|---|
| Δ6 desaturase | Synthetic gene (amino acid sequence from Synechocystis sp. PCC 6803) |
| ω3 desaturase | Synthetic gene (amino acid sequence from Synechococcus sp. PCC 7002). Also known as Δ15 desaturase. |
| Vipp1 | Vesicle-inducing protein in plastids. Important for synthesis of thylakoid membranes. Synthetic gene, amino acid sequence from Synechococcus sp. PCC 7002 |
| aadA | Aminoglycoside-3: adenyltransferase. Confers resistance to spectinomycin and streptomycin antibiotics. |
| lacI | A repressor protein introduced to allow control of protein expression from the trc promoter |
| Ori | Sequence used for replication of the plasmid DNA |

TABLE 1-continued

| Feature | Function |
|---|---|
| mobA, B, C and repA, B, C | Genes encoding proteins required for replication of the plasmid in cells |
| lacO | DNA sequence to which LacI binds and blocks transcription |
| AttB1, 2 | DNA sequences used or cloning genes into the pAM4418 expression plasmid |
| trpA and rrnB T2 terminators | DNA sequences that block continued transcription, helping to limit unwanted expression from the plasmid |
| SP6, T7 | DNA sequences used for PCR and sequencing |

II. Lipid Compositions and Profiles

Provided in accordance with some embodiments of the presently disclosed subject matter are lipid compositions comprising stearidonic acid, gammalinolenic acid (GLA), and/or 8,11,14,17 eicosatetraenoic acid (C20:4 ω3, or ω3 ETA). Stearidonic acid (SDA; C18:4, an omega-3 fatty acid) is a target for a nutraceutical. SDA is more stable than DHA and EPA (longer shelf life, higher quality pure product). Additionally, because it bypasses the mammalian delta-6 desaturase, SDA is much more efficiently converted to the longer chain omega-3 PUFAs (compared to its precursor, alpha-linolenic acid, ALA). Human and animal studies reveal that SDA has a variety of health benefits, including reducing inflammation, hyperlipidemia, obesity and suppressing the growth of breast cancer (Whelan, J Nutr., January 2009 January, 139(1):5-10).

Gamma-linolenic acid (GLA, 18:3 ω6) is an omega-6, 18-carbon PUFA found in human milk and several botanical seed oils (borage [~21% GLA], black currant [~17% GLA] and evening primrose [~9% GLA]), and is typically consumed as a part of a dietary supplement. Numerous in vitro and in vivo animal models have shown that GLA-supplemented diets attenuate various inflammatory responses (Sergeant et al., Eur J Pharmacol. 2016 Aug. 15; 785:77-86).

Omega-3 ETA (ω3 ETA) is a very rare 20-carbon fatty acid that has been shown to be a potent inhibitor of inflammatory mechanisms induced by its omega-6 counterpart, 5,8,11,14 eicosatetraenoic acid (or ω6 arachidonic acid). For example, it has been shown to inhibit enzymes involved in the uptake of ω6 arachidonic acid into cells and the metabolism of ω6 arachidonic acid to prostaglandins and thromboxanes via cyclooxygenase. See Simpoulos, Am. J Clin Nutr. 1991, 55:438-463; Ringborn et al., J Nat Prod. 2001 June; 64(6):745-9; and Neufeld et al., J. Lipid Res., 1984, 25:288-293. Consequently, it is a target for a therapeutic agent. For example, it has been suggested for use in the treatment of asthma. See U.S. Pat. No. 4,584,320, herein incorporated by reference in its entirety. Further, in some embodiments, lipid compositions in accordance with the presently disclosed subject matter are used as additives to food, including food for humans and for animal feed.

In some embodiments, a lipid composition having a particular lipid profile is provided. In some embodiments, a "profile" refers to a % of a given PUFA relative to the total fatty acid concentration or total ω3 fatty acid concentration. In some embodiments, a lipid composition is provided, having a lipid profile comprising at least about 8% (e.g., at least about 8, 10, 12, 14, 16, 18, 20, 21, 22, 23, or 24%) stearidonic acid (SDA). In some embodiments, a lipid composition is provided having a lipid profile comprising at least about 10% (e.g., at least about 10, 12, 14, 16, 18, 20, 21, 22, 23, 24, or 25%) GLA. In some embodiments, a lipid composition is provided having a lipid profile comprising at least about 9% (e.g., at least about 9, 10, 12, 14, 16, 18, 20, 21, 22, 23, 24, or 25%) ALA. In some embodiments, provided is a lipid composition with a lipid profile comprising at least one or more omega-3 (ω3) fatty acids selected from the group comprising α-linolenic acid (ALA), stearidonic acid (SDA), and/or ω3ETA, optionally wherein the lipid profile comprises at least about 23%, at least about 24%, at least about 25%, at least about 30%, or at least about 35% of the ω3 fatty acids. In some embodiments the lipid profile comprises at least about 9% ALA, at least about 15% (e.g., 16%, 17%, 18%, 19%, 20%, 21%, 22%, 23%, or 24% SDA, and/or any detectable amount of ω3 ETA, such as at least about 1, 2, 3, 4, or 5% ω3 ETA. In some embodiments, a lipid composition having a lipid profile comprising at least about 25% or more α-linolenic acid (ALA), and optionally, a lipid profile comprising at least about 33% or more ALA, is provided. In some embodiments, a lipid composition is provided having any detectable amount of ω3 ETA, such as at least about 1, 2, 3, 4, 5, 6, 7, 8, 9 or 10% ω3 ETA, including 4-10% ω3 ETA.

In some embodiments, a lipid composition in accordance with the presently disclosed subject matter has a lipid profile characterized by a significant amount of ω3 PUFAs conjugated to polar lipids, such as phospholipids and/or glycolipids. In some embodiments, the glycolipids are present in a greater amount than other lipids such as phospholipids and triglycerides.

The fatty acyl chains of monogalactosyl diglycerides (MGDG) and digalactosyl diglycerides (DGDG) can contain PUFAs (including ω3 FAs) in cyanobacteria. MGDG and DGDG are more soluble and can be extracted by supercritical fluid extraction. Importantly, recent human studies show ω3 PUFAs in galactolipids are more bioavailable in humans than phospholipids found in Krill oils. See Kagan et al., Lipids in Heath and Disease, 12: 102 (2013). In some embodiments, lipids in a lipid composition of the presently disclosed subject matter are ω3 PUFAs complexed to DGDG and/or to MGDG.

In some embodiments, a lipid composition in accordance with the presently disclosed subject matter is produced by a modified microorganism. In some embodiments, the microorganism is a cyanobacterium, a diverse phylum of oxygenic phototrophs in the kingdom bacteria. In some embodiments, the cyanobacterium is in the order Gloeobacterales. In some embodiments, the cyanobacterium is in the order Chroococcales. In some embodiments, the cyanobacterium is in the order Nostocales. In some embodiments, the cyanobacterium is in the order Oscillatoriales. In some embodiments, the cyanobacterium is in the order Pleurocapsales. In some embodiments, the cyanobacterium is in the order Prochlorales. In some embodiments, the cyanobacterium is in the order Stigonematales. In some embodiments, the cyanobacterium is unicellular. In some embodiments, the cyanobacterium is filamentous heterocystous. In some embodiments, the cyanobacterium is filamentous non-heterocystous. In some embodiments, the cyanobacterium is a freshwater strain. In some embodiments, the cyanobacterium is a marine strain. In some embodiments, the cyanobacterium is a species of *Anabaena*, *Leptolyngbya*, *Lyngbya*, *Nostoc* (e.g., *Nostoc commune*), *Phormidium* (e.g., *Phormidium valderianum*), *Spirulina*, *Synechococcus* or *Synechocystis*.

III. Modified Microorganisms

In some embodiments, the presently disclosed subject matter provides a modified microorganism, for example an engineered cyanobacterium, as a source of ω3 PUFAs and omega-6 PUFAs, such as but not limited to ALA, SDA and ETAω3. In some embodiments, the modified microorganism comprises a recombinant vector in accordance with the presently disclosed subject matter. In some embodiments, a modified microorganism in accordance with the presently disclosed subject matter comprises a first exogenous gene encoding thylakoid-promoting protein Vipp1, wherein the modified microorganism further comprises at least a second exogenous gene encoding a desaturase; wherein the modified microorganism produces a lipid in a greater amount than does a control microorganism identical in all respects except that it does not include the first exogenous gene encoding thylakoid-promoting protein Vipp1 and the second exogenous gene encoding a desaturase. In some embodiments, the modified microorganism comprises at least two exogenous genes encoding a desaturase, wherein each gene encodes a different desaturase. In some embodiments, the desaturase is a Δ6 desaturase or an ω3 desaturase. In some embodiments, the first desaturase is a Δ6 desaturase and the second desaturase is an ω3 desaturase. In some embodiments, the various gene constructs as disclosed herein are integrated into the host genome.

In some embodiments, the nucleic acid sequence encoding a thylakoid-promoting protein Vipp1, the nucleic acid sequence encoding a Δ6 desaturase, and/or the nucleic acid sequence encoding an ω3 desaturase is a natural gene sequence. In some embodiments, the nucleic acid sequence encoding a thylakoid-promoting protein Vipp1, the nucleic acid sequence encoding a Δ6 desaturase, and/or the nucleic acid sequence encoding an ω3 desaturase is a synthetic gene sequence.

In some embodiments, the thylakoid-promoting protein Vipp1, Δ6 desaturase, and/or ω3 desaturase is/are homologous with respect to the modified microorganism. In some embodiments, the thylakoid-promoting protein Vipp1, Δ6 desaturase, and/or ω3 desaturase is/are heterologous with respect to the modified microorganism.

In some embodiments, the thylakoid-promoting protein Vipp1 is encoded by a nucleic acid sequence comprising SEQ ID NO: 1, or by a coding sequence comprising a nucleotide sequence that is 70%, 75%, 80%, 85%, 90%, 91%, 92%, 93%, 94%, 95%, 96%, 97%, 98% or 99% identical to SEQ ID NO: 1 and/or any nucleic acid sequence that encodes SEQ ID NO:6 or an amino acid sequence at least about 70%, 75%, 80%, 85%, 90%, 91%, 92%, 93%, 94%, 95%, 96%, 97%, 98% or 99% identical to SEQ ID NO:6. In some embodiments, the desaturase is encoded by a nucleic acid sequence comprising a sequence selected from the group comprising SEQ ID NOs: 2 and 3, or by a coding sequence comprising a nucleotide sequence that is 70%, 75%, 80%, 85%, 90%, 91%, 92%, 93%, 94%, 95%, 96%, 97%, 98% or 99% identical to SEQ ID NOs: 2 or 3 and/or to a nucleic acid sequence that encodes SEQ ID NO:5 or SEQ ID NO7 or an amino acid sequence at least about 70%, 75%, 80%, 85%, 90%, 91%, 92%, 93%, 94%, 95%, 96%, 97%, 98% or 99% identical to SEQ ID NO:5 or SEQ ID NO:7. In some embodiments, the thylakoid-promoting protein Vipp1, Δ6 desaturase, and 03 desaturase are each encoded by a nucleic acid sequence comprising SEQ ID NO: 4 or by a coding sequence comprising a nucleotide sequence that is 70%, 75%, 80%, 85%, 90%, 91%, 92%, 93%, 94%, 95%, 96%, 97%, 98% or 99% identical to SEQ ID NO: 4. In some embodiments, the Vipp1, Δ6 desaturase and ω3 desaturase are each encoded by another nucleic acid that encodes each of SEQ ID NO:6, SEQ ID NO: 5, and SEQ ID NO: 7, wherein the coding sequences for SEQ ID NOs: 6, 5, and 7 are arranged in any order within the larger sequence.

In some embodiments, a lipid composition in accordance with the presently disclosed subject matter is produced by a modified microorganism. In some embodiments, the microorganism is a cyanobacterium, a diverse phylum of oxygenic phototrophs in the kingdom bacteria. In some embodiments, the cyanobacterium is in the order Gloeobacterales. In some embodiments, the cyanobacterium is in the order Chroococcales. In some embodiments, the cyanobacterium is in the order Nostocales. In some embodiments, the cyanobacterium is in the order Oscillatoriales. In some embodiments, the cyanobacterium is in the order Pleurocapsales. In some embodiments, the cyanobacterium is in the order Prochlorales. In some embodiments, the cyanobacterium is in the order Stigonematales. In some embodiments, the cyanobacterium is unicellular. In some embodiments, the cyanobacterium is filamentous heterocystous. In some embodiments, the cyanobacterium is filamentous non-heterocystous. In some embodiments, the cyanobacterium is a freshwater strain. In some embodiments, the cyanobacterium is a marine strain. In some embodiments, the cyanobacterium is a species of *Anabaena, Leptolyngbya, Lyngbya, Nostoc* (e.g., *Nostoc commune*), *Phormidium* (e.g., *Phormidium valderianum*), *Spirulina, Synechococcus* or *Synechocystis*.

In some embodiments, modified microorganisms in accordance with the presently disclosed subject matter are used as nutraceuticals (including but not limited to pharmaceuticals, dietary supplements, medical foods and functional foods) and/or additives to food, including food for humans and for animal feed (e.g., feed for fish, such as Tilapia, and/or for other animals, such as fowl, swine and cattle). Thus, in some embodiments, the modified microorganisms can be use in aquaculture. Representative formulation techniques and administration approaches are disclosed in U.S. Pat. No. 8,343,753, which is incorporated herein by reference in its entirety.

IV. Methods of Production and Use

In some embodiments, the presently disclosed subject matter provides a method of culturing a lipid-producing microorganism. In some embodiments, the method comprises: providing a culture of a modified microorganism that comprises an exogenous gene encoding thylakoid-promoting protein Vipp1 and at least one exogenous gene encoding a desaturase in a suitable culture medium under conditions in which the exogenous gene encoding the thylakoid-promoting protein Vipp1 and the exogenous gene encoding the desaturase are expressed. In some embodiments, the culture produces a greater amount and a greater proportion of selected ω6 PUFAs such as GLA and ω3 PUFAs such as ALA, SDA, and ETAω3 than does a culture comprising a control microorganism identical in all respects except that it does not include the exogenous gene encoding the thylakoid-promoting protein Vipp1 and at least one exogenous gene encoding a desaturase. In some embodiments, the modified microorganism comprises a recombinant vector in accordance with the presently disclosed subject matter.

In some embodiments, the modified microorganism comprises at least two exogenous genes encoding a desaturase, wherein each gene encodes a different desaturase. In some embodiments the first desaturase is Δ6 desaturase and the second desaturase is a ω3 desaturase.

In some embodiments, the nucleic acid sequence encoding a thylakoid-promoting protein Vipp1, the nucleic acid sequence encoding a Δ6 desaturase, and/or the nucleic acid sequence encoding a ω3 desaturase is a natural gene sequence. In some embodiments, the nucleic acid sequence encoding a thylakoid-promoting protein Vipp1, the nucleic acid sequence encoding a Δ6 desaturase, and/or the nucleic acid sequence encoding an 03 desaturase is a synthetic gene sequence.

In some embodiments, the thylakoid-promoting protein Vipp1, Δ6 desaturase, and/or ω3 desaturase is/are homologous with respect to the modified microorganism. In some embodiments, the thylakoid-promoting protein Vipp1, Δ6 desaturase, and/or ω3 desaturase is/are heterologous with respect to the modified microorganism.

In some embodiments, the thylakoid-promoting protein Vipp1 is encoded by a nucleic acid sequence comprising SEQ ID NO: 1, or by a coding sequence comprising a nucleotide sequence that is 70%, 75%, 80%, 85%, 90%, 91%, 92%, 93%, 94%, 95%, 96%, 97%, 98% or 99% identical to SEQ ID NO: 1 and/or by a coding sequence comprising a nucleic acid sequence that encodes an amino acid sequence comprising SEQ ID NO: 6 or an amino acid sequence at least about 70%, 75%, 80%, 85%, 90%, 91%, 92%, 93%, 94%, 95%, 96%, 97%, 98% or 99% identical to SEQ ID NO:6. In some embodiments, the desaturase is encoded by a nucleic acid sequence comprising a sequence selected from the group comprising SEQ ID NOs: 2 and 3, or by a coding sequence comprising a nucleotide sequence that is 70%, 75%, 80%, 85%, 90%, 91%, 92%, 93%, 94%, 95%, 96%, 97%, 98% or 99% identical to SEQ ID NOs: 2 or 3. In some embodiments, the desaturase is encoded by a coding sequence comprising a nucleic acid sequence that encodes an amino acid sequence comprising SEQ ID NO:5 or SEQ ID NO:7 or an amino acid sequence at least about 70%, 75%, 80%, 85%, 90%, 91%, 92%, 93%, 94%, 95%, 96%, 97%, 98% or 99% identical to SEQ ID NO:5 or SEQ ID NO:7. In some embodiments, the thylakoid-promoting protein Vipp1, Δ6 desaturase, and ω3 desaturase are each encoded by a nucleic acid sequence comprising SEQ ID NO: 4 or by a coding sequence comprising a nucleotide sequence that is 70%, 75%, 80%, 85%, 90%, 91%, 92%, 93%, 94%, 95%, 96%, 97%, 98% or 99% identical to SEQ ID NO: 4. In some embodiments, the Vipp1, Δ6 desaturase and ω3 desaturase are each encoded by a coding sequence comprising a nucleic acid that encodes each of SEQ ID NO:6, SEQ ID NO: 5, and SEQ ID NO: 7, or an amino acid sequence at least about 70%, 75%, 80%, 85%, 90%, 91%, 92%, 93%, 94%, 95%, 96%, 97%, 98% or 99% identical to SEQ ID NO:6, SEQ ID NO:5 or SEQ ID NO:7, wherein the respective coding sequences for a particular polypeptide are arranged in any order within the larger sequence.

In some embodiments, the modified microorganism is a cyanobacterium, a diverse phylum of oxygenic phototrophs in the kingdom bacteria. In some embodiments, the cyanobacterium is in the order Gloeobacterales. In some embodiments, the cyanobacterium is in the order Chroococcales. In some embodiments, the cyanobacterium is in the order Nostocales. In some embodiments, the cyanobacterium is in the order Oscillatoriales. In some embodiments, the cyanobacterium is in the order Pleurocapsales. In some embodiments, the cyanobacterium is in the order Prochlorales. In some embodiments, the cyanobacterium is in the order Stigonematales. In some embodiments, the cyanobacterium is unicellular. In some embodiments, the cyanobacterium is filamentous heterocystous. In some embodiments, the cyanobacterium is filamentous non-heterocystous. In some embodiments, the cyanobacterium is a freshwater strain. In some embodiments, the cyanobacterium is a marine strain. In some embodiments, the cyanobacterium is a species of

*Anabaena, Leptolyngbya, Lyngbya, Nostoc* (e.g., *Nostoc commune*), *Phormidium* (e.g., *Phormidium valderianum*), *Spirulina, Synechococcus* or *Synechocystis*.

In some embodiments, the method further comprises extracting a lipid composition from the culture. In some embodiments, a modified microorganism (or a processed product and/or extract thereof) and/or a lipid composition in accordance with the presently disclosed subject matter can be used as a food product, a dietary supplement, a medical food, a nutraceutical, a pharmaceutical, a functional food or animal feed additive.

Also provided in accordance with the presently disclosed subject matter are compositions, methods, and kits for the prophylactic and/or therapeutic treatment of a disease or condition, in particular a cardiovascular or inflammatory disease or a condition involving a psychological or neurodevelopmental disorder. Representative formulation techniques and administration approaches are disclosed in U.S. Pat. No. 8,343,753, which is incorporated herein by reference in its entirety.

As used herein, the phrase "therapeutically effective amount" refers to an amount of a compound or composition that is sufficient to produce the desired effect, which can be a therapeutic or agricultural effect. The therapeutically effective amount will vary with the application for which the compound or composition is being employed, the microorganism and/or the age and physical condition of the subject, the severity of the condition, the duration of the treatment, the nature of any concurrent treatment, the pharmaceutically or agriculturally acceptable carrier used, and like factors within the knowledge and expertise of those skilled in the art. An appropriate "therapeutically effective amount" in any individual case can be determined by one of ordinary skill in the art by reference to the pertinent texts and literature and/or by using routine experimentation. (See, for example for pharmaceutical applications, *Remington, The Science And Practice of Pharmacy* (9th Ed. 1995).)

The presently disclosed subject matter additionally provides methods for treating a mammalian disease in a subject in need thereof by administration to said subject a therapeutically effective amount of the compositions of the presently disclosed subject matter. In some embodiments, the mammalian diseases that are treated include, but are not limited to, cardiovascular diseases and inflammatory diseases. In other embodiments, the cardiovascular diseases to be treated include, but are not limited to, hypertriglyceridemia, coronary heart disease, stroke, acute myocardial infarction and atherosclerosis. In further embodiments, the inflammatory diseases to be treated include, but are not limited to, asthma, arthritis, allergic rhinitis, psoriasis, atopic dermatitis, inflammatory bowel diseases, Alzheimer's disease, Crohn's disease, and allergic rhinoconjunctitis. In additional embodiments, the mammalian diseases to be treated include psychiatric disorders. Psychiatric disorders include, but are not limited to, depression, bipolar disorder, schizophrenia. In addition, the compositions of the presently disclosed subject matter can be used to maintain and/or enhance cognitive function and prevent and/or treat brain inflammation.

As used herein, the term "subject" refers to any animal (e.g., avian, fish or mammal), including, but not limited to, humans, non-human primates, birds, and the like, which is to be the recipient of a particular treatment. The terms "subject" and "patient" are used interchangeably herein, such as but not limited to a mammalian or avian subject. Illustrative avians according to the presently disclosed subject matter include chickens, ducks, turkeys, geese, quail, pheasant, ratites (e.g., ostrich), domesticated birds (e.g., parrots and *canaries*), and birds in ovo. Fish of the presently disclosed subject matter include, but are not limited to, salmon, tilapia, carp, trout, bream, catfish, bass, sturgeon, and the like. Mammals of the presently disclosed subject matter include, but are not limited to, canines, felines, bovines, caprines, equines, ovines, porcines, rodents (e.g. rats and mice), lagomorphs, primates (including non-human primates), humans, and the like, and mammals in utero. Any mammalian subject in need of being treated according to the presently disclosed subject matter is suitable. According to some embodiments of the presently disclosed subject matter, the mammal is a non-human mammal. In some embodiments, the mammal is a human subject. Mammalian subjects of both genders and at any stage of development (i.e., neonate, infant, juvenile, adolescent, adult) can be treated according to the presently disclosed subject matter.

V. Examples

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

The Examples below describe the engineering of various microorganisms in accordance with the presently disclosed subject matter. To alter the fatty acid and more particularly the PUFA profile of a microorganism, microorganisms can be genetically modified wherein endogenous or exogenous lipid biosynthesis pathway enzymes are expressed or overexpressed. Steps to genetically engineer a microbe to alter its fatty acid profile as to the degree and location in the carbon backbone of fatty acid unsaturation and to decrease or increase fatty acid chain length comprise the design and construction of a transformation vector (e.g., a plasmid), transformation of the microbe with one or more vectors, selection of transformed microbes (transformants), growth of the transformed microbe, and analysis of the fatty acid profile and distribution of complex lipids produced by the engineered microbe.

Genomic DNA from *Shewanella woodyi* is purchased from the American Type Culture Collection, then PCR is used to amplify the regions of interest (ORFs 2 and 8, of 833 and 1631 bp, respectively, are individually amplified; ORFs 5, 7 and 8 are in tandem on a single 16.6 kb of DNA and are amplified in 4 fragments). Each PCR fragment includes a slightly overlapping segment with respect to the next fragment so that they can be mixed together with linearized plasmid vector, annealed, ligated and transformed into *E. coli* (or done in a more stepwise fashion). For enhancing stability of this bacterial plasmid containing a relatively large "cargo", a low copy number plasmid is employed for the initial cloning steps. The construct is sequenced in its entirety to ensure that there are no mistakes; if there are, additional PCR is conducted to replace "cassettes" within the DNA or mutagenesis is conducted to generate the wild type sequence. Incorporation of plasmid into *Leptolyngbya* sp. is confirmed by PCR, and samples are tested for EPA and other fatty acid synthesis as described elsewhere herein.

"Starting" cyanobacteria: *Synechocystis* sp. PCC 6803 has the Δ6 desaturase gene, but does not grow very quickly. *Synechococcus* sp. PCC 7002 does not have the Δ6 desaturase gene, but does have the ω3 desaturase gene, and is touted to grow as fast as 2 hr doubling time. However, this strain was not so "fast growing". To modify the PUFA content, cyanobacteria were modified by the overexpression of acyl-lipid desaturase genes, and a thylakoid membrane synthesis control protein (where PUFAs and photosynthetic complexes are localized).

Three target genes for expression/overexpression in cyanobacteria:
1. Acyl-lipid Δ6-desaturase from *Synechocystis* sp. PCC 6803
2. Acyl-lipid ω3 desaturase from *Synechococcus* sp. PCC 7002
3. Vipp1 from *Synechococcus* sp. PCC 7002

The genes encoding these 3 proteins were synthesized by GenScript, with their codon usage optimized by GenScript for expression in *E. coli*. These genes were supplied in a generic cloning vector, pUC57. In addition to the three synthetic genes, two expression vectors were also employed, one each for the PCC 6803 Δ6-desaturase and PCC 7002 Vipp1, constructed in the same way as described for the synthetic genes, but using the native sequence of the genes. These were generated by PCR amplification of the genes from genomic DNA.

The host cyanobacterial strains used for engineered expression of the target genes are *Leptolyngbya* sp. strain BL0902 (Taton et al, (2012), PLoS 7(1):e30901) and *Anabaena* sp. strain PCC 7120, because they typically are used for molecular biology/bioengineering and have been observed to grow well. *Leptolyngbya* sp. strain BL0902 was chosen due to its use in the Taton et al. (2012) paper describing the molecular biology tools developed for bioengineering of this cyanobacterium (especially the expression plasmid pAM4418, see below).

The expression vector used was pAM4418 described by Taton et al (2012). pAM4418 is a broad host range, *E. coli*-cyanobacteria shuttle plasmid that confers resistance to streptomycin and spectinomycin, and contains both the lacI$^q$ repressor and the trc promoter from *E. coli*. The plasmid contains a Gateway recombination cassette, which allows for gene transfer from a Gateway donor plasmid, placing the gene under the control of the trc promoter. Taton et al (2012) showed that the trc promoter was active in Leptolyngba BL0902, but expression was not controlled by the lac repressor, that is, expression appeared to be constitutive.

The genes for synthetic Δ6 desaturase and wω3 desaturase were amplified from the GenScript clones by PCR using primers which added the sequence CACC before the initiating ATG codon. This allows directional cloning of the PCR product into the Gateway donor plasmid, pENTR/SD/D-topo (Invitrogen), which provides an upstream Shine-Dalgarno sequence (ribosome-binding site) that is known to function in cyanobacteria. The downstream primers for both genes contained XhoI restriction sites; in combination with an AscI site in the pENTR/SD/D-topo plasmid this allows for addition of the vipp1 gene following the desaturase gene. The vipp1 gene synthesized by Genscript contains a XhoI site at the 5' end and HindIII plus AscI sites at the 3' end. After digestion with Xho1 and Asc1, the vipp1 gene was cloned following the desaturase genes in the pENTR/SD/D-topo clones.

In order to create a donor plasmid containing both Δ6 and ω3 desaturase genes and vipp1, the ω3 desaturase gene was PCR amplified from the original pUC57 clone using a 5' primer containing HindIII site plus a ribosome-binding site in combination with a 3' primer containing an Asc1 restriction site. The PCR product was digested with HindIII and AscI and ligated into the pENTR/SD/D-topo clone containing genes to express Δ6 desaturase and Vipp1, digested with the same two restriction enzymes.

Seven (7) pENTR/SD/D-topo clones were prepared for testing:
1. Δ6-desaturase
2. ω3 desaturase
3. Δ6 desaturase+Vipp1
4. 3 desaturase+Vipp1
5. Δ6 desaturase+Vipp+ω3 desaturase
6. native PCC 6803 Δ6 desaturase
7. native PCC 7002 Vipp1

The inserts of all 7 plasmids were sequenced and the genes found to have the correct sequences. The inserts from these 7 plasmids were transferred into the *E. coli*-cyanobacterial shuttle expression vector pAM4418 using the Gateway recombination system (Invitrogen) based on the site-specific recombination system of lambda bacteriophage. This was achieved using Invitrogen's LR Clonase II Enzyme Mix. The resultant pAM4418 clones were screened by restriction digest to identify the correct plasmids.

These plasmids were then used to transform *E. coli* DH10B cells containing the conjugal plasmid, pRL443 and the helper plasmid, pRL623. These resulting strains were grown overnight in rich LB media, washed with fresh LB media and finally resuspended in BG-11 media (media that is used for growth of the two cyanobacteria in this report) as a 10-fold concentrated stock. Cultures of the two cyanobacteria were grown to late exponential phase, harvested by centrifugation and washed twice with fresh BG-11 media, before resuspension as a 4-fold concentrated stock. These cyanobacterial suspensions were treated for 10 min in a sonicator bath to reduce the length of the multicellular strands, before being mixed with aliquots of the DH10B transformants. The cell mixtures were centrifuged, resuspended in 200 μL of BG-II media and incubated for 1 hour at 30° C., before being spread on an agar plate containing BG-11 and 5% LB. After 24 hours incubation in low light at 30° C., the cells were washed off and spread on selective plates containing 2 μg/mL spectinomycin and streptomycin. After 7-10 days incubation at 30° C. under illumination, single colonies were restreaked on to a fresh BG-11/spectinomycin/streptomycin plate and incubated for 5-7 days. A scrape of colonies was used to inoculate 30 mL of BG-11 in a 250 mL conical flask, and grown for 5 days at 30° C., with shaking at 120 rpm, and illumination. Cultures were harvested by centrifugation (5,000 rpm for 10 min), and the pellets stored frozen at −80° C. The cell pellets were dried by lyophilization before the analysis of lipid content.

Figure 3:
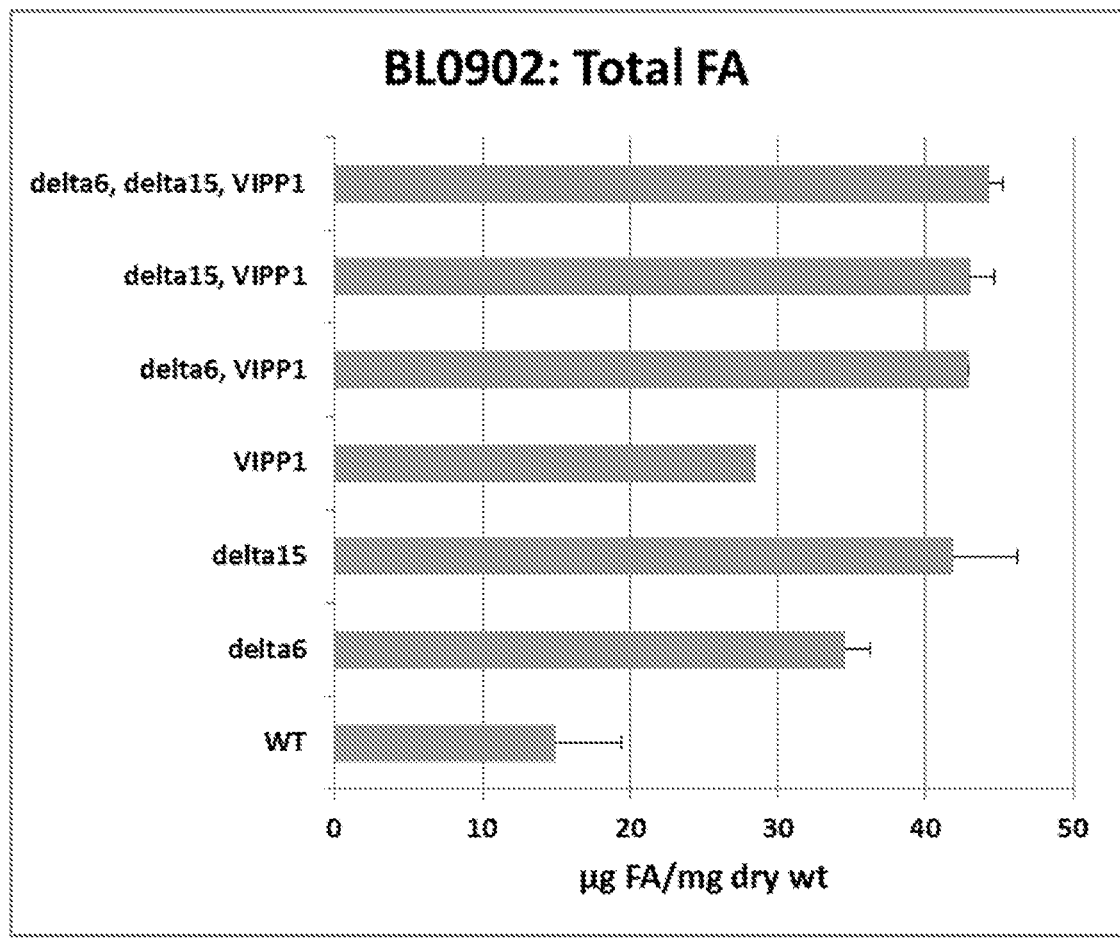
FIG. 3 is a graph showing the total fatty acid (FA) concentrations (in micrograms per milligram of dry weight (big/mg) produced in modified cyanobacteria strains. Total FAs are shown for a cyanobacterium transformed with a plasmid containing one or more structural genes to express the delta 6 (Δ6) desaturase, or the delta 15 (Δ15 also known as ω3) desaturase, or Vipp1, or combinations of delta 6/Vipp1, of delta 15/Vipp1, or of delta 6/delta 15/Vipp1 proteins. In these plasmids, the introduced genes were engineered to express protein sequences corresponding to the Δ6 desaturase from *Synechocystis* sp. PCC 6803, the Δ15 (ω3) desaturase from *Synechococcus* sp. PCC 7002, and/or the thylakoid-promoting protein Vipp1 from *Synechococcus* sp. PCC 7002. Also shown is the total FA concentration from the parent cyanobacterial species *Leptolyngbya* sp. BL0902 (WT). The number (n) of independent experiments used to generate the data is given for each construct in the lower panel.
Figure 4:
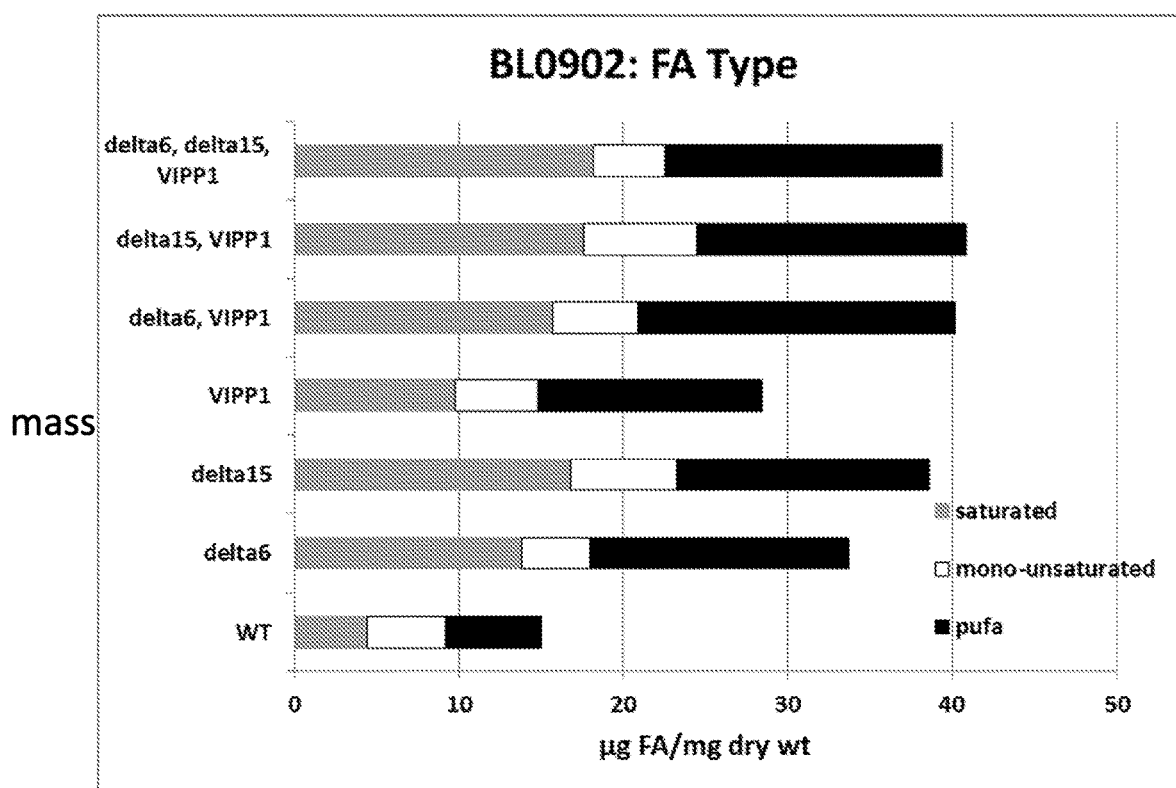
FIG. 4 is a graph showing the concentrations of classes (saturated, monounsaturated, or polyunsaturated) of fatty acids in wild-type (WT) and transgenic *Leptolyngbya* sp. BL0902 cyanobacteria. The transgenic bacteria include bacteria transformed (plasmids identical to those used in FIG. 3) with a plasmid expressing the delta 6 desaturase enzyme (delta6), the delta 15 desaturase enzyme (delta15 also ω3), the thylakoid-promoting protein Vipp1 (VIPP1), a combination of the delta 6 desaturase enzyme and the Vipp1 protein (delta6, VIPP1), a combination of the delta 15 desaturase enzyme and the Vipp1 protein (delta15, VIPP1), or a combination of the delta 6 desaturase enzyme, the delta 15 desaturase enzyme and the Vipp1 protein (delta6, delta15, VIPP1). The delta-15 desaturase is more correctly termed an ω3 desaturase as the target site for the introduced double bond is 3 carbons from the methyl end of fatty acids. The enzyme is also called the delta15 desaturase, referencing the standard C-18 fatty acid, but the enzyme recognizes the methyl end of the fatty acid unlike the delta-6 desaturase, for example, which recognizes the carboxyl end.

Lipid content data are presented in FIGS. 3-7. FIG. 3 shows that introduction of the genes expressing delta 6 desaturase, the ω3 desaturase (delta 15), Vipp1 or gene combinations (delta 6, Vipp1; delta 15, Vipp1; delta 6, delta 15, Vipp1) markedly increased the concentration of total fatty acids within the bacteria. FIG. 4 illustrates that introduction of the genes to express delta 6 desaturase, the ω3 desaturase (delta 15), or Vipp1, or combinations of these genes (delta 6, Vipp1; delta 15, Vipp1; delta 6, delta 15, Vipp1) elevated the concentrations of polyunsaturated fatty acids (PUFAs) within the bacteria.

Figure 5A:
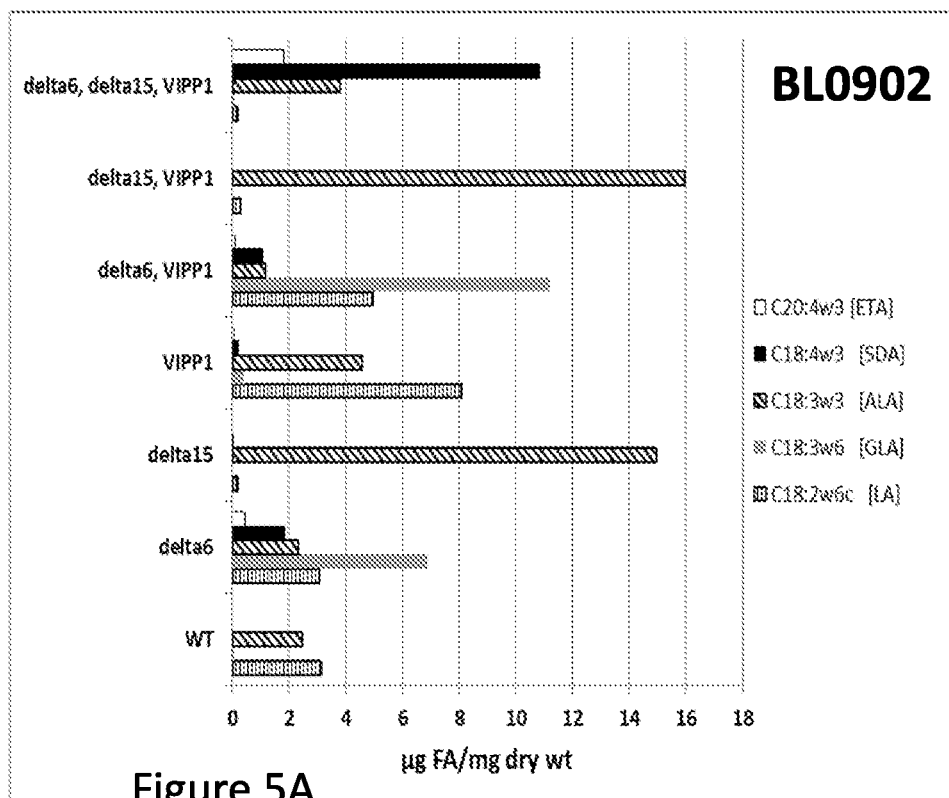
FIG. 5A is a graph showing the polyunsaturated fatty acid (PUFA) concentrations (mass per dry weight (μg/mg)) produced by wild-type (WT) and transgenic *Leptolyngbya* sp. BL0902 cyanobacteria. The transgenic bacteria include bacteria transformed (plasmids identical to those used in FIGS. 3 and 4) with a plasmid expressing the delta 6 desaturase enzyme (delta6), the delta 15 desaturase enzyme (delta15), the thylakoid promoting protein Vipp1 (VIPP1), a combination of the delta 6 desaturase enzyme and the Vipp1 protein (delta6, VIPP1), a combination of the delta 15 desaturase enzyme and Vipp1 (delta15, VIPP1), and a combination of the delta 6 desaturase enzyme, the delta 15 desaturase enzyme and Vipp1 (delta6, delta15, VIPP1).
Figure 5B:
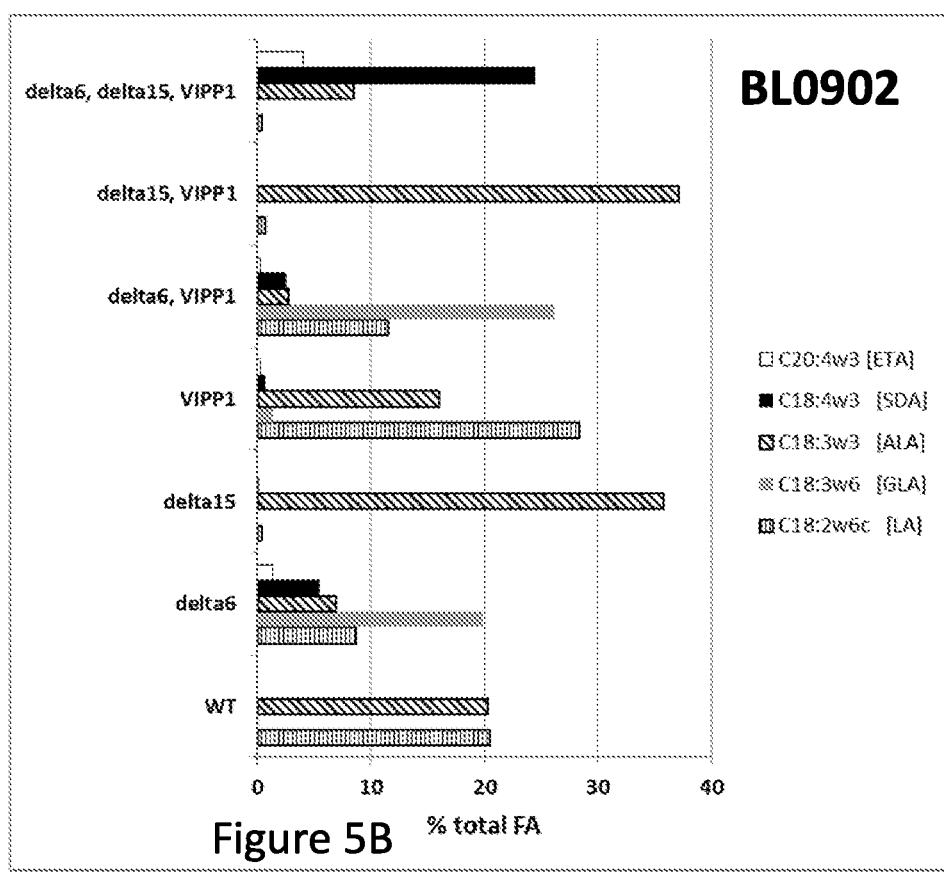
FIG. 5B is a graph showing PUFA production from the wild-type *Leptolyngbya* sp. BL0902 cyanobacteria and the aforementioned transgenic combinations. However, in this case, the data is expressed as % of a given PUFA relative to the total fatty acid concentration.

Results from the examination of the impact of the introduced genes and gene combinations on the distribution of specific ω3 and ω6 PUFAs are shown in FIG. 5. The parental strain contained almost equal amounts of the 18 carbon omega-6 precursor, linoleic acid (LA; 18:2ω6) and the ω3 precursor alpha linolenic acid (ALA; 18:3ω3), but has little or none of the delta 6 desaturase products (SDA or GLA). Upon introduction of the native Δ6 desaturase (derived from clone 6, above), the SDA and GLA content of the bacteria dramatically increased at the expense of the ALA and LA precursor content. Expression of the omega-3 methyl end desaturase (aka Δ15 desaturase) dramatically increased the ALA content suggesting that the overexpression was driving conversion of LA to ALA. Expression of the thylakoid-promoting protein Vipp1 (derived from clone 7, above) surprisingly generated more unsaturated fatty acids, especially LA providing more substrate to the Δ6 and ω3 desaturases. In addition, it was found that far more of ω3 fatty acid was in SDA rather than ALA, indicating that bacteria expressing all three genes (Δ6+Δ15+Vipp1) produced the most desired product for the reasons discussed above.

|  | Relative Amount (%) (Δ6 + Δ15 + Vipp1) |
| --- | --- |
| ALA (18:3) | 8.53 ± 0.31 |
| SDA (18:4) | 24.4 ± 0.81 |
| Total ALA + SDA | 32.93 |

This finding was surprising because there remains a great deal of controversy as to the actual role of Vipp1 in cyanobacteria, plants and other microorganisms. It is known to be a lipid transfer protein and has been suggested to enhance the production of thylakoid membranes but has not been shown to affect the level of fatty acid unsaturation in cells.

Expression of Vipp1 and delta 6 desaturase produced a bacterium highly enriched in GLA. Expression of Vipp1 and delta 15 desaturase produced a bacterium highly enriched in ALA. The combination of all three genes expressed from a single plasmid produced bacteria highly enriched in omega-3 PUFAs including ALA, SDA, and ω3ETA, with a particular enrichment in SDA. Interestingly, almost 5% of the total fatty acids was ETAω3. ETAω3 is extremely promising as a therapeutic, but extremely rare in nature.

Figure 6A:
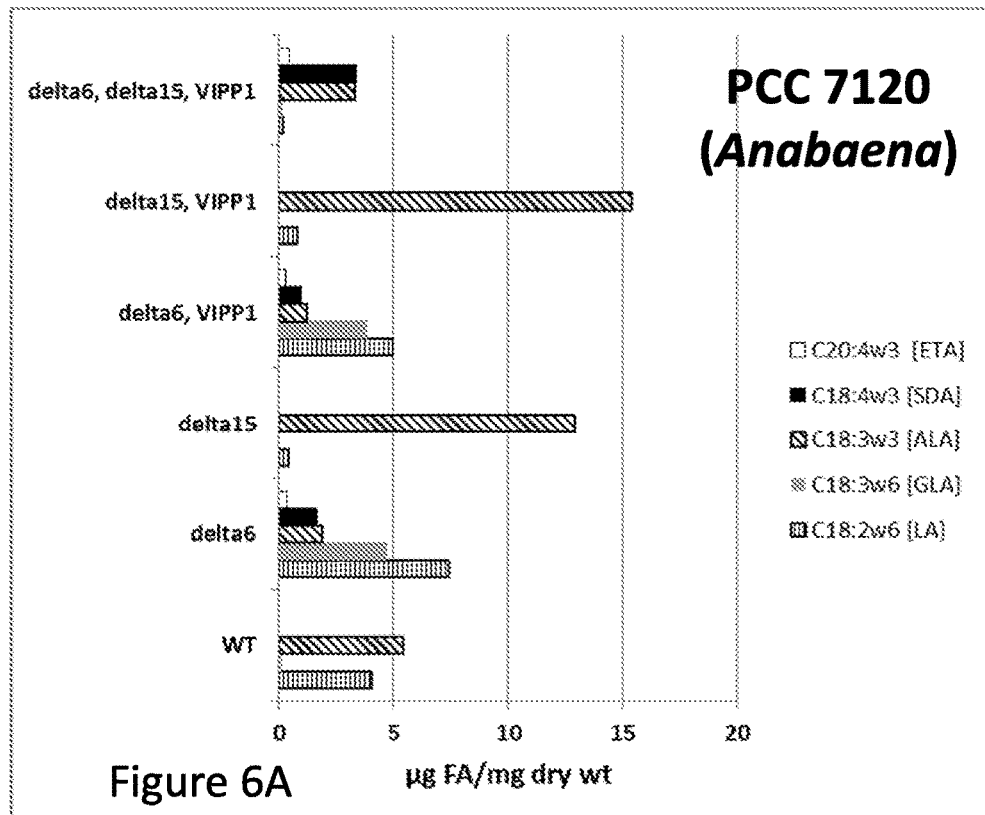
FIGS. 6A and 6B are a pair of graphs showing the concentrations of individual PUFAs expressed as mass per dry weight (μg/mg; 6A) or % of total FAs (6B) produced by wild-type (WT) and transgenic Anabaena sp. PCC7120 cyanobacteria. Plasmids introduced into the Anabaena sp. cyanobacteria are identical to those used in Leptolyngbya sp. BL0902 cyanobacteria as shown in FIGS. 3-5. The transgenic bacteria include bacteria transformed with a plasmid expressing the delta 6 desaturase enzyme (delta6), the delta 15 desaturase enzyme (delta15), a combination of the delta 6 desaturase enzyme and the thylakoid-promoting protein Vipp1 (delta6, VIPP1), a combination of the delta 15 desaturase enzyme and Vipp1 (delta15, VIPP1), and a combination of the delta 6 desaturase enzyme, the delta 15 desaturase enzyme and Vipp1 (delta6, delta15, VIPP1).
Figure 6B:
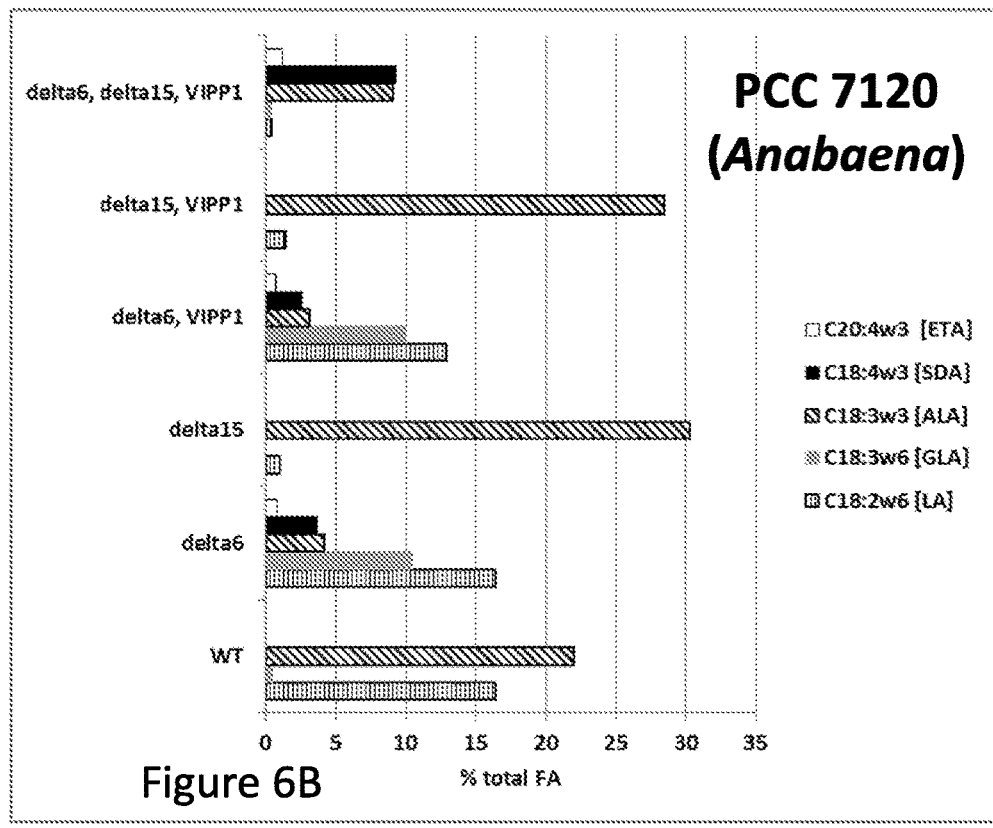

Anabaena sp. strain PCC 7120 was also analyzed, and it was found that the expression of these same genes and gene combinations induced very similar PUFA profiles to those of BL0902 (FIG. 6).

Figure 7:
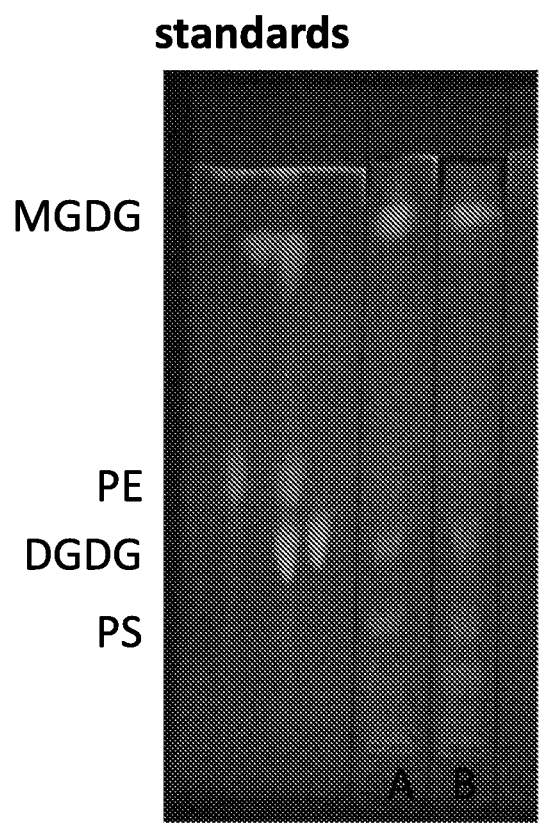
FIG. 7 shows thin layer chromatography analysis of the wild type (WT, "A") and the delta 6, delta 15, and Vipp1 transgenic strain of BL0902 (+Δ6, Δ15, VIPP1, "B"). These indicate that the bacteria contain a high abundance of glycolipids including the galactolipids, mono (MGDG)- and digalactosyl-diglycerides (DGDG).

FIG. 7 shows the distribution of complex lipids including glycerolipids and glycolipids. These data indicated that a large proportion of the lipids in the parental strain and the triple gene-expressing strain reside in mono (MGDG)- and digalactosyl-diglycerides (DGDG), and addition of the three genes does not fundamentally alter the relative distribution of ω3 PUFAs in complex lipids within the bacteria.

After separation of these species by thin layer chromatography (FIG. 7), fatty acid compositions were measured in the manner described above. Unexpectedly, the majority of the ALA and SDA present in the engineered bacteria expressing all three genes (Δ6+Δ15+Vipp1) was found in MGDG, and little in DGDG, PS, or PE. This result indicates that the majority of ALA and SDA are present in the highly bioavailable monogalactosyldiglycerides, not in DGDG, phospholipids or triglycerides.

Sequences of Cyanobacterial Genes—Protein-Encoding Sequences are Upper Case:

Synthetic Acyl-lipid Δ6-desaturase gene
SEQ ID NO: 2
catATGCTGACGGCAGAACGTATCAAGTTTACCCAGAAGCGTGGCTTTCG

TCGTGTCCTGAACCAACGTGTGGATGCGTATTTTGCTGAACATGGTCTGA

CCCAGCGTGATAACCCGTCAATGTATCTGAAAACGCTGATTATCGTCCTG

TGGCTGTTCTCGGCGTGGGCCTTTGTGCTGTTCGCACCGGTTATTTTCC

GGTCCGCCTGCTGGGTTGCATGGTTCTGGCAATCGCTCTGGCGGCCTTTT

CATTCAATGTCGGCCATGATGCAAACCACAATGCTTATAGCTCTAACCCG

CATATTAATCGTGTTCTGGGCATGACCTACGACTTCGTCGGTCTGAGTTC

CTTTCTGTGGCGTTATCGCCACAACTACCTGCATCACACCTATACGAATA

TTCTGGGCCATGATGTGGAAATCCACGGCGACGGTGCCGTTCGTATGAGC

CCGGAACAGGAACATGTGGGTATCTACCGCTTTCAGCAATTCTATATTTG

GGGCCTGTACCTGTTTATCCCGTTCTATTGGTTTCTGTATGATGTCTACC

TGGTGCTGAACAAAGGTAAGTACCATGACCACAAAATTCCGCCGTTTCAA

CCGCTGGAACTGGCATCTCTGCTGGGCATCAAGCTGCTGTGGCTGGGCTA

TGTGTTCGGTCTGCCGCTGGCGCTGGGCTTTTCAATTCCGGAAGTCCTGA

TCGGTGCCTCGGTGACCTATATGACGTACGGCATTGTGGTTTGTACCATC

TTCATGCTGGCTCATGTTCTGGAAAGCACCGAATTTCTGACGCCGGATGG

CGAATCTGGTGCAATTGATGACGAATGGGCTATTTGCCAGATCCGTACCA

CGGCGAACTTCGCCACCAACAATCCGTTCTGGAACTGGTTTTGTGGCGGT

CTGAATCACCAAGTGACGCATCACCTGTTTCCGAACATTTGCCATATCCA

CTATCCGCAGCTGGAAAACATCATCAAGGACGTTTGTCAAGAATTCGGTG

TGGAATATAAAGTTTACCCGACCTTTAAGGCAGCTATTGCGAGTAATTAC

CGCTGGCTGGAAGCGATGGGCAAGGCCTCCTAA

Synthetic Acyl-lipid ω3 desaturase gene
SEQ ID NO: 3
ATGCAATCCACCGTTCGTTCTCCGGGTAGCCGTGAAAGCCTGCGCCAAGA

CCTGCCGTTTACGCTGAAAGACGTGAAAGCCGCCATTCCGGATTATTGCT

TCCAGCCGAGCGTGTTTCGTTCTCTGGCGTACTTTTTCCTGGATATCGGT

ATTATCGCAGGCCTGTATGCTATTGCGGCCTACCTGGACTCTTGGTTTTT

CTATCCGATCTTTTGGTTCGCACAGGGTACGATGTTTGGGCTCTGTTCG

TGGTTGGCCATGATTGTGGCCACGGTAGCTTCTCTCGCAGTAAATTTCTG

AACGACCTGATCGGTCATCTGAGCCACACCCCGATTCTGGTTCCGTTTCA

TGGCTGGCGTATTTCACACCGCACCCATCACTCGAACACGGGTAATATCG

ATACCGACGAAAGCTGGTATCCGATTCCGGAATCTAAATACGATCAGATG

GGCTTCGCGGAAAAACTGGTCCGTTTTTATGCGCCGCTGATTGCCTATCC

GATCTACCTGTTTAAACGCAGTCCGGGTCGTGGTCCGGGTTCCCATTTCT

CACCGAAATCGCCGCTGTTTAAACCGGCGGAACGCAATGATATTATCCTG

TCCACGGCAGCTATTATCGCCATGGTCGGTTTTCTGGGCTGGTTCACCGT

GCAATTTGGTCTGCTGGCCTTCGTTAAATTTTATTTCGTCCCGTACGTGA

TTTTTGTTATCTGGCTGGATCTGGTTACGTATCTGCATCACACCGAAGCA

GACATCCCGTGGTACCGTGGTGATGACTGGTATTACCTGAAAGGCGCTCT

GAGTACCATTGATCGCGACTATGGTATTTTCAACGAAATCCATCACAATA

TTGGCACGCATGTCGCCCATCACATCTTTCACACCATTCCGCATTACCAC

-continued
CTGAAAGATGCGACCGAAGCCATCAAACCGCTGCTGGGCGACTATTACCG

TGTGAGCCATGCACCGATTTGGCGTAGCTTTTTCCGCTCCCAGAAAGCGT

GTCACTACATCGCCGACCAAGGCAGCCACCTGTATTATCAACCGAAAAAA

TAA

Synthetic Vipp1—SEQ ID NO: 1 ctcgagtaaactttactgtcgttttgttagctaaaaggaaaaaattATGG

GCTTCCTGGACCGTCTGGGCCGTGTCGTGAAAGCGAACCTGAATGATATG

GTGTCGAAAGCAGAAGACCCGGAAAAAATCCTGGAACAGGCAGTCGCTGA

TATGGGCGAAAGCCTGGTCCAACTGCGTCAGTCTGTGGCGCGTGCGATTG

CGGCCCAGAAGAAAACCGAACAGCAACTGATCAAAAACCAAACCGAAGCG

ACCACGTGGCAGAAGAAAGCGGAACTGGCCATTAAAAATGGTCGTGAAGA

TCTGGCACGCGAAGCTCTGGTTCGTAAGAAAACCTTTGCAGACACGGCAG

CTGTCCTGCAGCAACAGCTGACGCAACAGAACGCCCAAGTTAAAACCCTG

AAAGAAAATCTGCTGGCACTGGAAAGTAAAATCCAGGAAGCTAAAACCAA

GAAAGATATGCTGAAAGCACGCGCTAACGCGGCCAAAGCGAATGCCCAAC

TGCAGAGTACGATGAACAATATTGATACCAGCTCTGCGATGTCCGCCTTT

GAACGTATGGAAGACAAAATCATGGAACTGGAAGCACAGTCTGAAGCTAC

CAACGTGCTGGGCAGTGCGTCCCTGGATCAAGAATTCGCGCAGCTGGAAG

CCTCAAATTCGATTGATGACGAACTGGCCATGCTGAAAGCAGCTTCACAG

GAAGCACCGGCTCTGGAAGCGGCCAAAATGGTTGATGAAATGGAAGAAGT

GTCGGACACCCCGGTTGAAACGCCGGAACCGACCGACGCGGACTTTGCGG

CTGTTGATGCGGAACTGGAAGCACTGCGTACCCAGATGAAAAACCTGTAA aagcttggcgcgcc

For expression of all three genes:

Δ6 Desaturase+Vipp1+ω3 Desaturase Construction—
SEQ ID NO: 4

The restriction enzyme sites used for the construction are in bolded double underlined and in italics.

Sub-sequence including the coding sequence for Δ6
desaturase (i.e. 4-1084 of SEQ ID NO: 2),
ATGCTGACGGCAGAACGTATCAAGTTTACCCAGAAGCGTGGCTTTCGTCG

TGTCCTGAACCAACGTGTGGATGCGTATTTTGCTGAACATGGTCTGACCC

AGCGTGATAACCCGTCAATGTATCTGAAAACGCTGATTATCGTCCTGTGG

CTGTTCTCGGCGTGGGCCTTTGTGCTGTTCGCACCGGTTATTTTTCCGGT

CCGCCTGCTGGGTTGCATGGTTCTGGCAATCGCTCTGGCGGCCTTTTCAT

TCAATGTCGGCCATGATGCAAACCACAATGCTTATAGCTCTAACCCGCAT

ATTAATCGTGTTCTGGGCATGACCTACGACTTCGTCGGTCTGAGTTCCTT

TCTGTGGCGTTATCGCCACAACTACCTGCATCACACCTATACGAATATTC

TGGGCCATGATGTGGAAATCCACGGCGACGGTGCCGTTCGTATGAGCCCG

GAACAGGAACATGTGGGTATCTACCGCTTTCAGCAATTCTATATTTGGGG

CCTGTACCTGTTTATCCCGTTCTATTGGTTTCGTATGATGTCTACCTGG

TGCTGAACAAAGGTAAGTACCATGACCACAAAATTCCGCCGTTTCAACCG

CTGGAACTGGCATCTCTGCTGGGCATCAAGCTGCTGTGGCTGGGCTATGT

GTTCGGTCTGCCGCTGGCGCTGGGCTTTTCAATTCCGGAAGTCCTGATCG

GTGCCTCGGTGACCTATATGACGTACGGCATTGTGGTTTGTACCATCTTC

ATGCTGGCTCATGTTCTGGAAAGCACCGAATTTCTGACGCCGGATGGCGA

ATCTGGTGCAATTGATGACGAATGGGCTATTTGCCAGATCCGTACCACGG

CGAACTTCGCCACCAACAATCCGTTCTGGAACTGGTTTTGTGGCGGTCTG

AATCACCAAGTGACGCATCACCTGTTTCCGAACATTTGCCATATCCACTA

TCCGCAGCTGGAAAACATCATCAAGGACGTTTGTCAAGAATTCGGTGTGG

AATATAAAGTTTACCCGACCTTTAAGGCAGCTATTGCGAGTAATTACCGC

TGGCTGGAAGCGATGGGCAAGGCCTCCTAAagctcgagtaaactttactg tcgttttgttagctaaaagga

Sub-sequence including the coding sequence for
Vipp1 (i.e. 47-849 of SEQ ID NO: 1),
aaaaattATGGGCTTCCTGGACCGTCTGGGCCGTGTCGTGAAAGCGAACC

TGAATGATATGGTGTCGAAAGCAGAAGACCCGGAAAAAATCCTGGAACAG

GCAGTCGCTGATATGGGCGAAAGCCTGGTCCAACTGCGTCAGTCTGTGGC

GCGTGCGATTGCGGCCCAGAAGAAAACCGAACAGCAACTGATCAAAAACC

AAACCGAAGCGACCACGTGGCAGAAGAAAGCGGAACTGGCCATTAAAAAT

GGTCGTGAAGATCTGGCACGCGAAGCTCTGGTTCGTAAGAAAACCTTTGC

AGACACGGCAGCTGTCCTGCAGCAACAGCTGACGCAACAGAACGCCCAAG

TTAAAACCCTGAAAGAAAATCTGCTGGCACTGGAAAGTAAAATCCAGGAA

GCTAAAACCAAGAAAGATATGCTGAAAGCACGCGCTAACGCGGCCAAAGC

GAATGCCCAACTGCAGAGTACGATGAACAATATTGATACCAGCTCTGCGA

TGTCCGCCTTTGAACGTATGGAAGACAAAATCATGGAACTGGAAGCACAG

TCTGAAGCTACCAACGTGCTGGGCAGTGCGTCCCTGGATCAAGAATTCGC

GCAGCTGGAAGCCTCAAATTCGATTGATGACGAACTGGCCATGCTGAAAG

CAGCTTCACAGGAAGCACCGGCTCTGGAAGCGGCCAAAATGGTTGATGAA

ATGGAAGAAGTGTCGGACACCCCGGTTGAAACGCCGGAACCGACCGACGC

GGACTTTGCGGCTGTTGATGCGGAACTGGAAGCACTGCGTACCCAGATGA

AAAACCTGTAA*aagctt*aaaatataa

Sub-sequence including the coding sequence for ω3
desaturase (i.e. 1-1053 of SEQ ID NO: 3),
gtaggagataaaaacATGCAATCCACCGTTCGTTCTCCGGGTAGCCGTGA

AAGCCTGCGCCAAGACCTGCCGTTTACGCTGAAAGACGTGAAAGCCGCCA

TTCCGGATTATTGCTTCCAGCCGAGCGTGTTTCGTTCTCTGGCGTACTTT

TTCCTGGATATCGGTATTATCGCAGGCCTGTATGCTATTGCGGCCTACCT

GGACTCTTGGTTTTTCTATCCGATCTTTTGGTTCGCACAGGGTACGATGT

TTTGGGCTCTGTTCGTGGTTGGCCATGATTGTGGCCACGGTAGCTTCTCT

CGCAGTAAATTTCTGAACGACCTGATCGGTCATCTGAGCCACACCCCGAT

TCTGGTTCCGTTTCATGGCTGGCGTATTTCACACCGCACCCATCACTCGA

ACACGGGTAATATCGATACCGACGAAAGCTGGTATCCGATTCCGGAATCT

AAATACGATCAGATGGGCTTCGCGGAAAAACTGGTCCGTTTTTATGCGCC

```
GCTGATTGCCTATCCGATCTACCTGTTTAAACGCAGTCCGGGTCGTGGTC

CGGGTTCCCATTTCTCACCGAAATCGCCGCTGTTTAAACCGGCGGAACGC

AATGATATTATCCTGTCCACGGCAGCTATTATCGCCATGGTCGGTTTTCT

GGGCTGGTTCACCGTGCAATTTGGTCTGCTGGCCTTCGTTAAATTTTATT

TCGTCCCGTACGTGATTTTTGTTATCTGGCTGGATCTGGTTACGTATCTG

CATCACACCGAAGCAGACATCCCGTGGTACCGTGGTGATGACTGGTATTA

CCTGAAAGGCGCTCTGAGTACCATTGATCGCGACTATGGTATTTTCAACG

AAATCCATCACAATATTGGCACGCATGTCGCCCATCACATCTTTCACACC

ATTCCGCATTACCACCTGAAAGATGCGACCGAAGCCATCAAACCGCTGCT

GGGCGACTATTACCGTGTGAGCCATGCACCGATTTGGCGTAGCTTTTTCC

GCTCCCAGAAAGCGTGTCACTACATCGCCGACCAAGGCAGCCACCTGTAT

TATCAACCGAAAAAATAAcggcgcgcc
```

Figure 8:
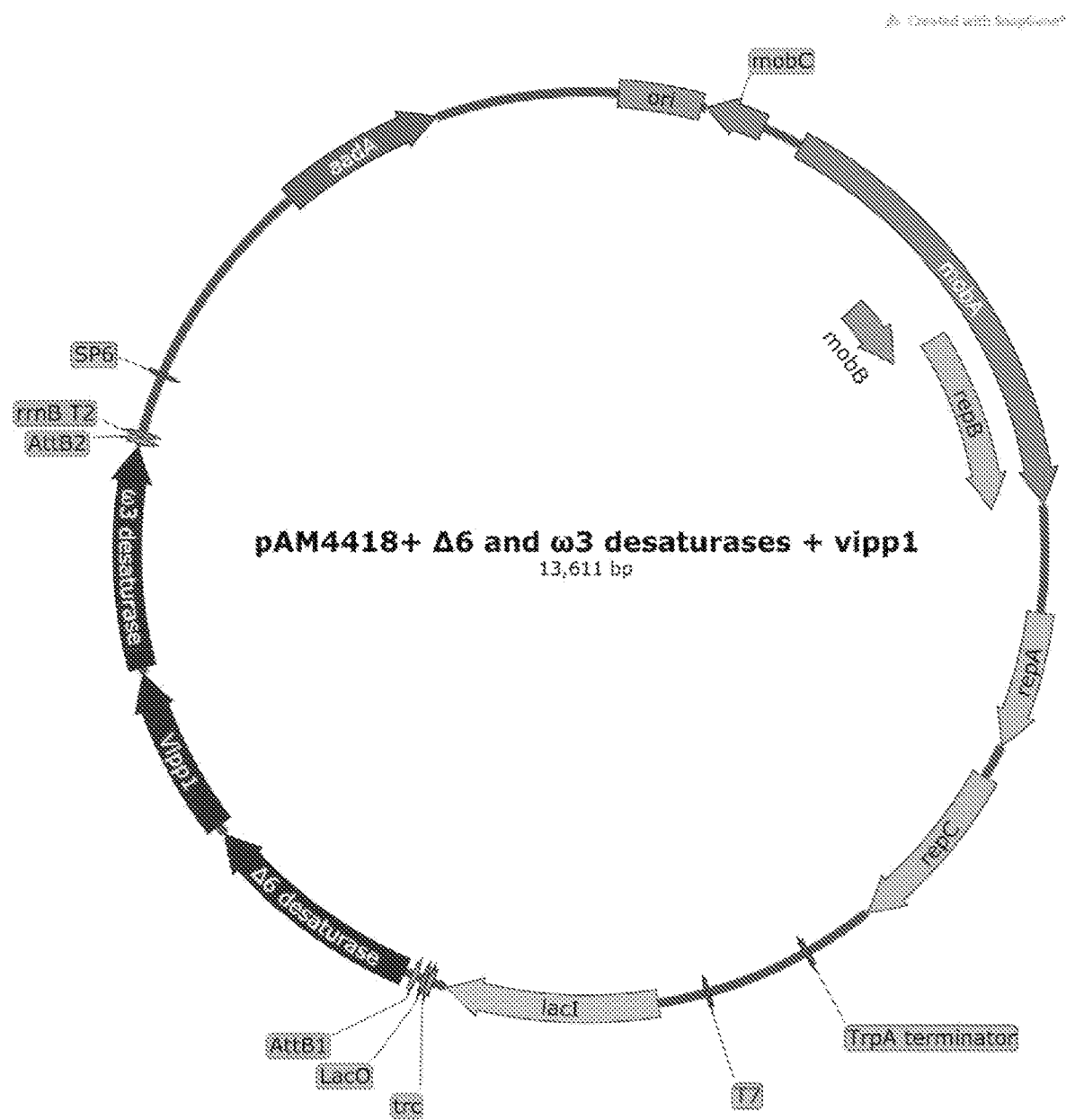
FIG. 8 is a plasmid map of the 13,611 basepair (bp) plasmid that includes the pAM44148 expression vector described in Taton et al. (2012) that contains both the lacI repressor gene and trc promoter from E. coli, as well as synthetic genes for expression of the delta 6 (Δ6) desaturase and omega 3 (ω3) desaturase (also referred to herein and in the Figures and text as delta 15 desaturase) and the vesicle-inducing protein in plasmids (Vipp1). As noted above, the delta-15 desaturase is more correctly termed an omega-3 desaturase as the target site for the introduced double bond is 3 carbons from the methyl end of the fatty acid. The enzyme is also called the delta15 desaturase, referencing the standard C-18 fatty acid, but the enzyme recognizes the methyl end of the fatty acid unlike the delta-6 desaturase, for example, which recognizes the carboxyl end.

SEQ ID NO:4 is an exemplary construction of a nucleic acid sequence that encodes each of the Δ6 desaturase, the ω3 desaturase, and Vipp1. See also FIG. 8. Other constructions can include the coding sequences for the two desaturases and vipp1 in other orders and/or with other non-coding intervening sequences. Other constructions can also include more than one copy of the coding sequence(s) of any or all of the Δ6 desaturase, the ω3 desaturase, and Vipp1.

Amino Acid Sequences:

```
Amino Acid Sequence for Synthetic Acyl-lipid Δ6
desaturase - SEQ ID NO: 5
MLTAERIKFT QKRGFRRVLN QRVDAYFAEH GLTQRDNPSM

YLKTLIIVLW LFSAWAFVLF APVIFPVRLL GCMVLAIALA

AFSFNVGHDA NHNAYSSNPH INRVLGMTYD FVGLSSFLWR

YRHNYLHHTY TNILGHDVEI HGDGAVRMSP EQEHVGIYRF

QQFYIWGLYL FIPFYWFLYD VYLVLNKGKY HDHKIPPFQP

LELASLLGIK LLWLGYVFGL PLALGFSIPE VLIGASVTYM

TYGIVVCTIF MLAHVLESTE FLTPDGESGA IDDEWAICQI

RTTANFATNN PFWNWFCGGL NHQVTHHLFP NICHIHYPQL

ENIIKDVCQE FGVEYKVYPT FKAAIASNYR WLEAMGKAS

Amino Acid Sequence for Synthetic Vipp1 - SEQ ID
NO 6:
MGFLDRLGRV VKANLNDMVS KAEDPEKILE QAVADMGESL

VQLRQSVARA IAAQKKTEQQ LIKNQTEATT WQKKAELAIK

NGREDLAREA LVRKKTFADT AAVLQQQLTQ QNAQVKTLKE

NLLALESKIQ EAKTKKDMLK ARANAAKANA QLQSTMNNID

TSSAMSAFER MEDKIMELEA QSEATNVLGS ASLDQEFAQL

EASNSIDDEL AMLKAASQEA PALEAAKMVD EMEEVSDTPV

ETPEPTDADF AAVDAELEAL RTQMKNL

Amino Acid Sequence for Synthetic Acyl-Lipid ω3
desaturase - SEQ ID NO: 7
MQSTVRSPGS RESLRQDLPF TLKDVKAAIP DYCFQPSVFR

SLAYFFLDIG IIAGLYAIAA YLDSWFFYPI FWFAQGTMFW

ALFVVGHDCG HGSFSRSKFL NDLIGHLSHT PILVPFHGWR

ISHRTHHSNT GNIDTDESWY PIPESKYDQM GFAEKLVRFY

APLIAYPIYL FKRSPGRGPG SHFSPKSPLF KPAERNDIIL

STAAIIAMVG FLGWFTVQFG LLAFVKFYFV PYVIFVIWLD

LVTYLHHTEA DIPWYRGDDW YYLKGALSTI DRDYGIFNEI

HHNIGTHVAH HIFHTIPHYH LKDATEAIKP LLGDYYRVSH

APIWRSFFRS QKACHYIADQ GSHLYYQPKK
```

All references listed herein, including patents, patent applications, data base citations and scientific literature, are incorporated herein by reference in their entireties to the extent that they supplement, explain, provide a background for, or teach methodology, techniques, and/or compositions employed herein.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A modified microorganism comprising:
   [i] a first exogenous gene encoding thylakoid-promoting protein Vipp1 having at least 70% sequence identity to SEQ ID NO: 6; and
   [ii] at least a second exogenous gene encoding a desaturase having at least 70% sequence identity to SEQ ID NO: 5 and/or SEQ ID NO: 7,
   wherein the modified microorganism produces a lipid in a greater amount than does a control microorganism identical in all respects except that it does not comprise the first exogenous gene encoding thylakoid-promoting protein Vipp1 and the at least a second exogenous gene encoding a desaturase.

2. The modified microorganism of claim 1, wherein the modified microorganism comprises at least two exogenous genes encoding a desaturase, wherein each gene encodes a different desaturase, and wherein the first desaturase is a Δ6 desaturase and the second desaturase is an 0 desaturase.

3. The modified microorganism of claim 1, wherein the thylakoid-promoting protein Vipp1, Δ6 desaturase, and ω3 desaturase are each encoded by a nucleic acid sequence comprising SEQ ID NO: 4 or a nucleic acid sequence at least 70% identical to SEQ ID NO: 4 or another nucleic acid sequence that encodes amino acid sequences comprising each of SEQ ID NOs: 5, 6, and 7 or amino acid sequences that are at least 70% identical to SEQ ID NOs: 5, 6, and 7.

4. The modified microorganism of claim 1, wherein the modified microorganism is a cyanobacterium, and wherein the cyanobacterium is a species of *Anabaena, Leptolyngbya, Lyngbya, Nostoc, Phormidium, Spirulina, Synechococcus* or *Synechocystis*.

5. A method of culturing a lipid-producing microorganism, the method comprising:
   culturing the modified microorganism of claim 1,
   wherein the culture produces a greater amount of the lipid than does a culture comprising a control microorganism identical in all respects except that it does not include the gene encoding an exogenous thylakoid-promoting protein Vipp1 and at least one exogenous gene encoding a desaturase.

6. The method of claim 5, wherein the modified microorganism comprises at least two exogenous genes encoding a desaturase, wherein each gene encodes a different desaturase, and wherein the first desaturase is a Δ6 desaturase and the second desaturase is a 0 desaturase.

7. The method of claim 6, wherein the thylakoid-promoting protein Vipp1, Δ6 desaturase, and ω3 desaturase are each encoded by a nucleic acid sequence comprising SEQ ID NO:4 or a nucleic acid sequence at least 70% identical to SEQ ID NO: 4 or a nucleic acid sequence that encodes amino acid sequences comprising each of SEQ ID Nos: 5, 6, and 7 or amino acid sequences at least 70% identical to SEQ ID NOs: 5, 6, and 7.

8. The method of claim 5, wherein the modified microorganism is a cyanobacterium, and wherein the cyanobacterium is a species of *Anabaena, Leptolyngbya, Lyngbya, Nostoc, Phormidium, Spirulina, Synechococcus* or *Synechocystis*.

9. The method of claim 5, further comprising extracting a lipid composition from the culture.

10. A composition comprising the microorganism of claim 1.

11. The composition of claim 10, wherein the composition is in an administrable form selected from the group consisting of a pharmaceutical formulation, a nutritional formulation, a feed formulation, a dietary supplement, a medical food, a functional food, a beverage product and combinations thereof.

12. The composition of claim 11, wherein the administrable form is a feed for use in aquaculture.

* * * * *

SEQUENCE LISTING

```
<160> NUMBER OF SEQ ID NOS: 7

<210> SEQ ID NO 1
<211> LENGTH: 864
<212> TYPE: DNA
<213> ORGANISM: Artificial Sequence
<220> FEATURE:
<223> OTHER INFORMATION: Artificially synthesized nucleotide sequence

<400> SEQUENCE: 1
ctcgagtaaa ctttactgtc gttttgttag ctaaaaggaa aaaattatgg gcttcctgga        60
ccgtctgggc cgtgtcgtga aagcgaacct gaatgatatg gtgtcgaaag cagaagaccc       120
ggaaaaaatc ctggaacagg cagtcgctga tatgggcgaa agcctggtcc aactgcgtca       180
gtctgtggcg cgtgcgattg cggcccagaa gaaaaccgaa cagcaactga tcaaaaacca       240
aaccgaagcg accacgtggc agaagaaagc ggaactggcc attaaaaatg gtcgtgaaga       300
```

```
tctggcacgc gaagctctgg ttcgtaagaa aacctttgca gacacggcag ctgtcctgca      360
gcaacagctg acgcaacaga acgcccaagt taaaaccctg aaagaaaatc tgctggcact      420
ggaaagtaaa atccaggaag ctaaaaccaa gaaagatatg ctgaaagcac gcgctaacgc      480
ggccaaagcg aatgcccaac tgcagagtac gatgaacaat attgatacca gctctgcgat      540
gtccgccttt gaacgtatgg aagacaaaat catggaactg gaagcacagt ctgaagctac      600
caacgtgctg ggcagtgcgt ccctggatca agaattcgcg cagctggaag cctcaaattc      660
gattgatgac gaactggcca tgctgaaagc agcttcacag gaagcaccgg ctctggaagc      720
ggccaaaatg gttgatgaaa tggaagaagt gtcggacacc ccggttgaaa cgccggaacc      780
gaccgacgcg gactttgcgg ctgttgatgc ggaactggaa gcactgcgta cccagatgaa      840
aaacctgtaa aagcttggcg cgcc                                            864
```

<210> SEQ ID NO 2
<211> LENGTH: 1083
<212> TYPE: DNA
<213> ORGANISM: Artificial Sequence
<220> FEATURE:
<223> OTHER INFORMATION: Artificially synthesized nucleotide sequence

<400> SEQUENCE: 2

```
catatgctga cggcagaacg tatcaagttt acccagaagc gtggctttcg tcgtgtcctg      60
aaccaacgtg tggatgcgta ttttgctgaa catggtctga cccagcgtga taacccgtca     120
atgtatctga aaacgctgat tatcgtcctg tggctgttct cggcgtgggc ctttgtgctg     180
ttcgcaccgg ttatttttcc ggtccgcctg ctggttgcaa tggttctggc aatcgctctg     240
gcggcctttt cattcaatgt cggccatgat gcaaaccaca atgcttatag ctctaacccg     300
catattaatc gtgttctggg catgacctac gacttcgtcg gtctgagttc ctttctgtgg     360
cgttatcgcc acaactacct gcatcacacc tatacgaata ttctgggcca tgatgtggaa     420
atccacggcg acggtgccgt tcgtatgagc ccggaacagg aacatgtggg tatctaccgc     480
tttcagcaat tctatatttg gggcctgtac ctgtttatcc cgttctattg gtttctgtat     540
gatgtctacc tggtgctgaa caaaggtaag taccatgacc acaaaattcc gccgtttcaa     600
ccgctggaac tggcatctct gctgggcatc aagctgctgt ggctgggcta tgtgttcggt     660
ctgccgctgg cgctgggctt ttcaattccg gaagtcctga tcggtgcctc ggtgacctat     720
atgacgtacg gcattgtggt ttgtaccatc ttcatgctgg ctcatgttct ggaaagcacc     780
gaatttctga cgccggatgg cgaatctggt gcaattgatg acgaatgggc tatttgccag     840
atccgtacca cggcgaactt cgccaccaac aatccgttct ggaactggtt tgtggcggt     900 ctgaatcacc aagtgacgca tcacctgttt ccgaacattt gccatatcca ctatccgcag     960
ctggaaaaca tcatcaagga cgtttgtcaa gaattcggtg tggaatataa agtttacccg    1020
acctttaagg cagctattgc gagtaattac cgctggctgg aagcgatggg caaggcctcc    1080
taa                                                                  1083
```

<210> SEQ ID NO 3
<211> LENGTH: 1053
<212> TYPE: DNA
<213> ORGANISM: Artificial Sequence
<220> FEATURE:
<223> OTHER INFORMATION: Artificially synthesized nucleotide sequence

<400> SEQUENCE: 3

```
atgcaatcca ccgttcgttc tccgggtagc cgtgaaagcc tgcgccaaga cctgccgttt      60
```

```
acgctgaaag acgtgaaagc cgccattccg gattattgct tccagccgag cgtgtttcgt    120
tctctggcgt acttttcct ggatatcggt attatcgcag gcctgtatgc tattgcggcc    180
tacctggact cttggttttt ctatccgatc ttttggttcg cacagggtac gatgttttgg    240
gctctgttcg tggttggcca tgattgtggc acggtagctc tctctcgcag taaatttctg    300
aacgacctga tcggtcatct gagccacacc ccgattctgg ttccgtttca tggctggcgt    360
atttcacacc gcacccatca ctcgaacacg gtaatatcg ataccgacga aagctggtat    420
ccgattccgg aatctaaata cgatcagatg ggcttcgcgg aaaaactggt ccgttttat    480
gcgccgctga ttgcctatcc gatctacctg tttaaacgca gtccgggtcg tggtccgggt    540
tcccatttct caccgaaatc gccgctgttt aaaccggcgg aacgcaatga tattatcctg    600
tccacggcag ctattatcgc catggtcggt tttctgggct ggttcaccgt gcaatttggt    660
ctgctggcct tcgttaaatt ttatttcgtc ccgtacgtga ttttgttat ctggctggat    720
ctggttacga atctgcatca caccgaagca gacatcccgt ggtaccgtgg tgatgactgg    780
tattacctga aaggcgctct gagtaccatt gatcgcgact atggtatttt caacgaaatc    840
catcacaata ttggcacgca gtcgcccat cacatctttc acaccattcc gcattaccac    900
ctgaaagatg cgaccgaagc catcaaaccg ctgctgggcg actattaccg tgtgagccat    960
gcaccgattt ggcgtagctt tttccgctcc cagaaagcgt gtcactacat cgccgaccaa   1020
ggcagccacc tgtattatca accgaaaaaa taa                                 1053

<210> SEQ ID NO 4
<211> LENGTH: 3025
<212> TYPE: DNA
<213> ORGANISM: Artificial Sequence
<220> FEATURE:
<223> OTHER INFORMATION: Artificially synthesized nucleotide sequence

<400> SEQUENCE: 4
atgctgacgg cagaacgtat caagtttacc cagaagcgtg gctttcgtcg tgtcctgaac    60
caacgtgtgg atgcgtattt tgctgaacat ggtctgaccc agcgtgataa cccgtcaatg   120
tatctgaaaa cgctgattat cgtcctgtgg ctgttctcgg cgtgggcctt tgtgctgttc   180
gcaccggtta ttttccggt ccgcctgctg ggttgcatgg ttctggcaat cgctctggcg   240
gccttttcat tcaatgtcgg ccatgatgca aaccacaatg cttatagctc taacccgcat   300
attaatcgtg ttctgggcat gacctacgac ttcgtcggtc tgagttcctt tctgtggcgt   360
tatcgccaca actacctgca tcacacctat acgaatattc tgggccatga gtggaaatc    420
cacggcgacg gtgccgttcg tatgagcccg gaacaggaac atgtgggtat ctaccgcttt   480
cagcaattct atatttgggg cctgtacctg tttatcccgt tctattggtt tctgtatgat   540
gtctacctgg tgctgaacaa aggtaagtac catgaccaca aaattccgcc gtttcaaccg   600
ctggaactgg catctctgct gggcatcaag ctgctgtggc tggctatgt gttcggtctg   660
ccgctggcgc tgggcttttc aattccggaa gtcctgatcg gtgcctcggt gacctatatg   720
acgtacggca ttgtggtttg taccatcttc atgctggctc atgttctgga aagcaccgaa   780
tttctgacgc cggatggcga atctggtgca attgatgacg aatgggctat ttgccagatc   840
cgtaccacgg cgaacttcgc caccaacaat ccgttctgga actggttttg tggcggtctg   900
aatcaccaag tgacgcatca cctgtttccg aacatttgcc atatccacta tccgcagctg   960
gaaaacatca tcaaggacgt tgtcaagaa ttcggtgtgg aatataaagt ttacccgacc  1020
```

```
tttaaggcag ctattgcgag taattaccgc tggctggaag cgatgggcaa ggcctcctaa      1080
agctcgagta aactttactg tcgttttgtt agctaaaagg aaaaaattat gggcttcctg      1140
gaccgtctgg gccgtgtcgt gaaagcgaac ctgaatgata tggtgtcgaa agcagaagac      1200
ccggaaaaaa tcctggaaca ggcagtcgct gatatgggcg aaagcctggt ccaactgcgt      1260
cagtctgtgg cgcgtgcgat tgcggcccag aagaaaaccg aacagcaact gatcaaaaac      1320
caaaccgaag cgaccacgtg gcagaagaaa gcggaactgg ccattaaaaa tggtcgtgaa      1380
gatctggcac gcgaagctct ggttcgtaag aaaacctttg cagacacggc agctgtcctg      1440
cagcaacagc tgacgcaaca gaacgcccaa gttaaaaccc tgaaagaaaa tctgctggca      1500
ctggaaagta aaatccagga agctaaaacc aagaaagata tgctgaaagc acgcgctaac      1560
gcggccaaag cgaatgccca actgcagagt acgatgaaca atattgatac cagctctgcg      1620
atgtccgcct ttgaacgtat ggaagacaaa atcatggaac tggaagcaca gtctgaagct      1680
accaacgtgc tgggcagtgc gtccctggat caagaattcg cgcagctgga agcctcaaat      1740
tcgattgatg acgaactggc catgctgaaa gcagcttcac aggaagcacc ggctctggaa      1800
gcggccaaaa tggttgatga atggaagaa gtgtcggaca ccccggttga aacgccggaa      1860
ccgaccgacg cggactttgc ggctgttgat gcggaactgg aagcactgcg tacccagatg      1920
aaaaacctgt aaaagcttaa aatataagta ggagataaaa acatgcaatc caccgttcgt      1980
tctccgggta gccgtgaaag cctgcgccaa gacctgccgt ttacgctgaa agacgtgaaa      2040
gccgccattc cggattattg cttccagccg agcgtgtttc gttctctggc gtactttttc      2100
ctggatatcg gtattatcgc aggcctgtat gctattgcgg cctacctgga ctcttggttt      2160
ttctatccga tcttttggtt cgcacagggt acgatgttt gggctctgtt cgtggttggc      2220
catgattgtg gccacggtag cttctctcgc agtaaatttc tgaacgacct gatcggtcat      2280
ctgagccaca ccccgattct ggttccgttt catggctggc gtatttcaca ccgcacccat      2340
cactcgaaca cggtaatat cgataccgac gaaagctggt atccgattcc ggaatctaaa      2400
tacgatcaga tgggcttcgc ggaaaaactg gtccgttttt atgcgccgct gattgcctat      2460
ccgatctacc tgtttaaacg cagtccgggt cgtggtccgg gttcccattt ctcaccgaaa      2520
tcgccgctgt ttaaaccggc ggaacgcaat gatattatcc tgtccacggc agctattatc      2580
gccatggtcg gttttctggg ctggttcacc gtgcaatttg gtctgctggc cttcgttaaa      2640
ttttatttcg tcccgtacgt gattttgtt atctggctgg atctggttac gtatctgcat      2700
cacaccgaag cagacatccc gtggtaccgt ggtgatgact ggtattacct gaaaggcgct      2760
ctgagtacca ttgatcgcga ctatggtatt ttcaacgaaa tccatcacaa tattggcacg      2820
catgtcgccc atcacatctt tcacaccatt ccgcattacc acctgaaaga tgcgaccgaa      2880
gccatcaaac cgctgctggg cgactattac cgtgtgagcc atgcaccgat tggcgtagc      2940 tttttccgct cccagaaagc gtgtcactac atcgccgacc aaggcagcca cctgtattat      3000
caaccgaaaa aataacgggc gcgcc                                            3025
```

<210> SEQ ID NO 5
<211> LENGTH: 359
<212> TYPE: PRT
<213> ORGANISM: Artificial Sequence
<220> FEATURE:
<223> OTHER INFORMATION: Amino acid sequence encoded by artificially
synthesized nucleotide sequence

<400> SEQUENCE: 5

Met Leu Thr Ala Glu Arg Ile Lys Phe Thr Gln Lys Arg Gly Phe Arg
1               5                   10                  15

Arg Val Leu Asn Gln Arg Val Asp Ala Tyr Phe Ala Glu His Gly Leu
            20                  25                  30

Thr Gln Arg Asp Asn Pro Ser Met Tyr Leu Lys Thr Leu Ile Ile Val
        35                  40                  45

Leu Trp Leu Phe Ser Ala Trp Ala Phe Val Leu Phe Ala Pro Val Ile
50                  55                  60

Phe Pro Val Arg Leu Leu Gly Cys Met Val Leu Ala Ile Ala Leu Ala
65                  70                  75                  80

Ala Phe Ser Phe Asn Val Gly His Asp Ala Asn His Asn Ala Tyr Ser
                85                  90                  95

Ser Asn Pro His Ile Asn Arg Val Leu Gly Met Thr Tyr Asp Phe Val
            100                 105                 110

Gly Leu Ser Ser Phe Leu Trp Arg Tyr Arg His Asn Tyr Leu His His
        115                 120                 125

Thr Tyr Thr Asn Ile Leu Gly His Asp Val Glu Ile His Gly Asp Gly
    130                 135                 140

Ala Val Arg Met Ser Pro Glu Gln Glu His Val Gly Ile Tyr Arg Phe
145                 150                 155                 160

Gln Gln Phe Tyr Ile Trp Gly Leu Tyr Leu Phe Ile Pro Phe Tyr Trp
                165                 170                 175

Phe Leu Tyr Asp Val Tyr Leu Val Leu Asn Lys Gly Lys Tyr His Asp
            180                 185                 190

His Lys Ile Pro Pro Phe Gln Pro Leu Glu Leu Ala Ser Leu Leu Gly
        195                 200                 205

Ile Lys Leu Leu Trp Leu Gly Tyr Val Phe Gly Leu Pro Leu Ala Leu
210                 215                 220

Gly Phe Ser Ile Pro Glu Val Leu Ile Gly Ala Ser Val Thr Tyr Met
225                 230                 235                 240

Thr Tyr Gly Ile Val Val Cys Thr Ile Phe Met Leu Ala His Val Leu
                245                 250                 255

Glu Ser Thr Glu Phe Leu Thr Pro Asp Gly Glu Ser Gly Ala Ile Asp
            260                 265                 270

Asp Glu Trp Ala Ile Cys Gln Ile Arg Thr Thr Ala Asn Phe Ala Thr
        275                 280                 285

Asn Asn Pro Phe Trp Asn Trp Phe Cys Gly Gly Leu Asn His Gln Val
        290                 295                 300

Thr His His Leu Phe Pro Asn Ile Cys His Ile His Tyr Pro Gln Leu
305                 310                 315                 320

Glu Asn Ile Ile Lys Asp Val Cys Gln Glu Phe Gly Val Glu Tyr Lys
                325                 330                 335

Val Tyr Pro Thr Phe Lys Ala Ala Ile Ala Ser Asn Tyr Arg Trp Leu
            340                 345                 350

Glu Ala Met Gly Lys Ala Ser
        355

<210> SEQ ID NO 6
<211> LENGTH: 267
<212> TYPE: PRT
<213> ORGANISM: Artificial Sequence
<220> FEATURE:
<223> OTHER INFORMATION: Amino acid sequence encoded by artificially
      synthesized nucleotide sequence

<400> SEQUENCE: 6

Met Gly Phe Leu Asp Arg Leu Gly Arg Val Val Lys Ala Asn Leu Asn
1               5                   10                  15

Asp Met Val Ser Lys Ala Glu Asp Pro Glu Lys Ile Leu Glu Gln Ala
            20                  25                  30

Val Ala Asp Met Gly Glu Ser Leu Val Gln Leu Arg Gln Ser Val Ala
        35                  40                  45

Arg Ala Ile Ala Ala Gln Lys Lys Thr Glu Gln Leu Ile Lys Asn
    50                  55                  60

Gln Thr Glu Ala Thr Thr Trp Gln Lys Lys Ala Glu Leu Ala Ile Lys
65                  70                  75                  80

Asn Gly Arg Glu Asp Leu Ala Arg Glu Ala Leu Val Arg Lys Lys Thr
                85                  90                  95

Phe Ala Asp Thr Ala Ala Val Leu Gln Gln Leu Thr Gln Gln Asn
            100                 105                 110

Ala Gln Val Lys Thr Leu Lys Glu Asn Leu Leu Ala Leu Glu Ser Lys
            115                 120                 125

Ile Gln Glu Ala Lys Thr Lys Lys Asp Met Leu Lys Ala Arg Ala Asn
130                 135                 140

Ala Ala Lys Ala Asn Ala Gln Leu Gln Ser Thr Met Asn Asn Ile Asp
145                 150                 155                 160

Thr Ser Ser Ala Met Ser Ala Phe Glu Arg Met Glu Asp Lys Ile Met
                165                 170                 175

Glu Leu Glu Ala Gln Ser Glu Ala Thr Asn Val Leu Gly Ser Ala Ser
            180                 185                 190

Leu Asp Gln Glu Phe Ala Gln Leu Glu Ala Ser Asn Ser Ile Asp Asp
        195                 200                 205

Glu Leu Ala Met Leu Lys Ala Ala Ser Gln Glu Ala Pro Ala Leu Glu
    210                 215                 220

Ala Ala Lys Met Val Asp Glu Met Glu Val Ser Asp Thr Pro Val
225                 230                 235                 240

Glu Thr Pro Glu Pro Thr Asp Ala Asp Phe Ala Ala Val Asp Ala Glu
                245                 250                 255

Leu Glu Ala Leu Arg Thr Gln Met Lys Asn Leu
            260                 265

<210> SEQ ID NO 7
<211> LENGTH: 350
<212> TYPE: PRT
<213> ORGANISM: Artificial Sequence
<220> FEATURE:
<223> OTHER INFORMATION: Amino acid sequence encoded by artificially
      synthesized nucleotide sequence

<400> SEQUENCE: 7

Met Gln Ser Thr Val Arg Ser Pro Gly Ser Arg Glu Ser Leu Arg Gln
1               5                   10                  15

Asp Leu Pro Phe Thr Leu Lys Asp Val Lys Ala Ile Pro Asp Tyr
            20                  25                  30

Cys Phe Gln Pro Ser Val Phe Arg Ser Leu Ala Tyr Phe Phe Leu Asp
        35                  40                  45

Ile Gly Ile Ile Ala Gly Leu Tyr Ala Ile Ala Ala Tyr Leu Asp Ser
    50                  55                  60

Trp Phe Phe Tyr Pro Ile Phe Trp Phe Ala Gln Gly Thr Met Phe Trp
65                  70                  75                  80

Ala Leu Phe Val Val Gly His Asp Cys Gly His Gly Ser Phe Ser Arg

```
                       85                  90                  95
Ser Lys Phe Leu Asn Asp Leu Ile Gly His Leu Ser His Thr Pro Ile
                100                 105                 110

Leu Val Pro Phe His Gly Trp Arg Ile Ser His Arg Thr His His Ser
                115                 120                 125

Asn Thr Gly Asn Ile Asp Thr Asp Glu Ser Trp Tyr Pro Ile Pro Glu
                130                 135                 140

Ser Lys Tyr Asp Gln Met Gly Phe Ala Glu Lys Leu Val Arg Phe Tyr
145                 150                 155                 160

Ala Pro Leu Ile Ala Tyr Pro Ile Tyr Leu Phe Lys Arg Ser Pro Gly
                165                 170                 175

Arg Gly Pro Gly Ser His Phe Ser Pro Lys Ser Pro Leu Phe Lys Pro
                180                 185                 190

Ala Glu Arg Asn Asp Ile Ile Leu Ser Thr Ala Ala Ile Ile Ala Met
                195                 200                 205

Val Gly Phe Leu Gly Trp Phe Thr Val Gln Phe Gly Leu Leu Ala Phe
                210                 215                 220

Val Lys Phe Tyr Phe Val Pro Tyr Val Ile Phe Val Ile Trp Leu Asp
225                 230                 235                 240

Leu Val Thr Tyr Leu His His Thr Glu Ala Asp Ile Pro Trp Tyr Arg
                245                 250                 255

Gly Asp Asp Trp Tyr Tyr Leu Lys Gly Ala Leu Ser Thr Ile Asp Arg
                260                 265                 270

Asp Tyr Gly Ile Phe Asn Glu Ile His His Asn Ile Gly Thr His Val
                275                 280                 285

Ala His His Ile Phe His Thr Ile Pro His Tyr His Leu Lys Asp Ala
    290                 295                 300

Thr Glu Ala Ile Lys Pro Leu Leu Gly Asp Tyr Tyr Arg Val Ser His
305                 310                 315                 320

Ala Pro Ile Trp Arg Ser Phe Phe Arg Ser Gln Lys Ala Cys His Tyr
                325                 330                 335

Ile Ala Asp Gln Gly Ser His Leu Tyr Tyr Gln Pro Lys Lys
                340                 345                 350
```